United States Patent [19]

Sano

[11] Patent Number: 5,615,680
[45] Date of Patent: Apr. 1, 1997

[54] METHOD OF IMAGING IN ULTRASOUND DIAGNOSIS AND DIAGNOSTIC ULTRASOUND SYSTEM

[75] Inventor: Akihiro Sano, Otawara, Japan

[73] Assignee: Kabushiki Kaisha Toshiba, Kanagawa-Ken, Japan

[21] Appl. No.: 505,540

[22] Filed: Jul. 21, 1995

[30] Foreign Application Priority Data

Jul. 22, 1994 [JP] Japan .................................. 6-171338

[51] Int. Cl.6 ...................................................... A61B 8/00
[52] U.S. Cl. ...................................................... 128/661.09
[58] Field of Search ........................ 128/660.04, 660.05, 128/661.08, 661.09, 661.1, 660.07, 661.04, 661.07

[56] References Cited

U.S. PATENT DOCUMENTS

| | | | |
|---|---|---|---|
| 5,285,788 | 2/1994 | Arenson et al. | 128/660.05 |
| 5,415,171 | 5/1995 | Goh et al. | 128/660.07 |
| 5,419,328 | 5/1995 | Goh et al. | 128/660.07 |

FOREIGN PATENT DOCUMENTS 6-114059  4/1994  Japan .

OTHER PUBLICATIONS

A.D. Fleming, et al., "Myocardial velocity gradients detected by Doppler imaging," The British Journal of Radiology, vol. 67, No. 799, 679–688, 1994.

Primary Examiner—George Manuel
Attorney, Agent, or Firm—Finnegan, Henderson, Farabow, Garrett & Dunner, L.L.P.

[57] ABSTRACT

A diagnostic ultrasound system comprising an element for detecting a velocity of motion of a tissue, such as a cardiac muscle or a vascular wall, contained in an object at every sampling point in a section of the object and an element for creating two-dimensionally mapped data of the velocity in the section. The system further comprises an element for analyzing a motion state of the tissue on the basis of local velocities falling into a plurality of local regions set on the two-dimensionally mapped data of the velocity and an element for displaying analysis results of the motion state. The velocity detecting element transmits an ultrasonic pulse signal toward the tissue in order to acquire a Doppler shifted echo, according to a pulsed Doppler technique.

37 Claims, 24 Drawing Sheets

SHORT-AXIS IMAGE
OF LEFT VENTRICLE

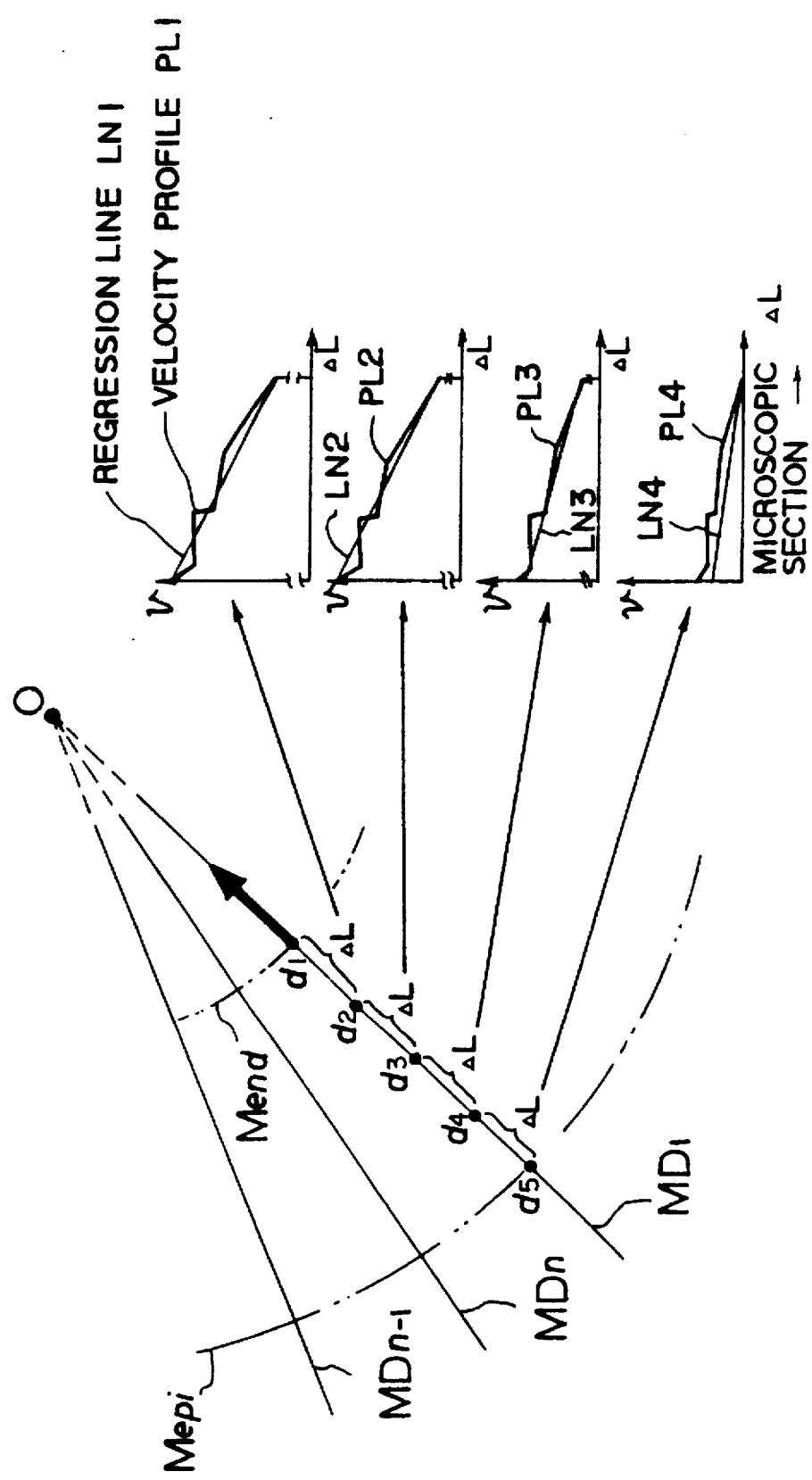

METHOD OF IMAGING IN ULTRASOUND DIAGNOSIS AND DIAGNOSTIC ULTRASOUND SYSTEM

BACKGROUND OF THE INVENTION

The present invention relates to a method of imaging in ultrasound diagnosis and diagnostic ultrasound system permitting effective diagnosis of ischemic cardiac disorders including myocardial infarction and angina pectoris, and left ventricular ectasia such as hypertrophic cardiomyophathy. More particularly, this invention is concerned with a diagnostic ultrasound system for tissue Doppler imaging (TDI) that detects velocities of motions made by the cardiac muscle (cardiac walls) or vascular walls using a Doppler imaging technique, computes various physical quantities related to the motions on the basis of the motion velocities, and displays the results of the computation in appropriate form.

DESCRIPTION OF THE RELATED ART

It has become essential for diagnosis of cardiac diseases to assess cardiac or vascular functions quantitatively. Various diagnostic methods have been devised.

In an ultrasonic approach, a B-mode tomographic image showing, for example, the left ventricle in real time is viewed in order to quantitatively evaluate the functions of the left ventricle (this is because the assessment of the cardiac functions depends mainly on the evaluation of the left ventricular functions). When symptoms such as ischemic cardiac disorders and left ventricular ectasia have progressed and become grave, this method of viewing enables diagnosis to some extent.

In recent years, some proposals have been made for a more advanced and specialized method of diagnosis. For example, there is a method of analyzing motions made by the left ventricular wall that is dedicated to diagnosis of ischemic cardiac disorders. This method is such that changes in thickness of the cardiac muscle of the left ventricle during systole and diastole are measured, and a region demonstrating a small change is evaluated as a "region with hyposystole" or a "ischemic region." Various algorithms have been devised for this analysis. Whichever algorithm is adopted, a B-mode tomographic image is used to trace the left ventricular endocardium or epicardium during systole and diastole. The trace information is used for measurements.

For diagnosing cardiac infarction, stress echocardiography is widely adopted. According to this method, the heart is stressed by means of exercises, medication, or electric stimulation, and ultrasound (B-mode) tomographic images of the heart produced before and after the heart is stressed are recorded. The images produced before and after the heart is stressed are then displayed side by side on a single monitor. Changes in thickness of the cardiac muscle occurring during systole and diastole (the cardiac muscle is normally thicker during systole) are then compared with each other in order to detect an infarcted region.

The aforesaid various methods of diagnosis have the drawbacks described below.

To begin with, diagnosis through viewing of a B-mode tomographic image will be discussed. Since a monitor screen merely shows a real-time image, it is difficult to determine hypofunction of an organ or recognize an anomalous tissue. In practice, even a physician having much experience finds it difficult to acquire detailed information concerning a region with hyposystole in a patient suffering from an ischemic cardiac disorder or concerning left ventricular ectasia. The method of analyzing motions made by the left ventricular wall is dedicated to diagnosis of ischemic cardiac disorders and is therefore not versatile.

For detecting objective diagnostic information concerning left ventricular ectasia, any effective and convenient method of diagnosis using a diagnostic ultrasound system has not been established yet.

SUMMARY OF THE INVENTION

The present invention attempts to overcome the aforesaid drawbacks lying in the conventional methods of diagnosis. A major object of the present invention is to provide a diagnostic ultrasound system permitting easy understanding of the kinetic state of an organ (tissue) or a region to be evaluated merely by viewing a display screen, and enabling quantitative, high-precision, and quick assessment of hypofunction or anomaly of the organ.

Another object of the present invention is to provide a diagnostic ultrasound system for issue Doppler imaging widely adaptable for evaluating the cardiac muscle, vascular walls, or any other locomotorium having a contraction center in not only a case with an ischemic cardiac disorder but also a case in which the motion velocity at an abnormal region differs from the one at a normal region.

Yet another object of the present invention is to provide a diagnostic ultrasound system obviating the necessity of stressing the heart for diagnosis and enabling diagnosis without causing patient discomfort.

For achieving the above objects, according to one aspect of the present invention, a diagnostic ultrasound system, comprising: means for detecting a velocity of motion of a tissue contained in an object at every sampling point in a section of the object; means for creating two-dimensionally mapped data of the velocity in the section; means for analyzing a motion state of the tissue on the basis of local velocities falling into a plurality of local regions set on the two-dimensionally mapped data of the velocity; and means for displaying analysis results of the motion state. Preferably, the velocity detecting means comprises a scanning means transmitting an ultrasonic pulse signal toward the tissue in order to acquire a Doppler shifted echo, according to a pulsed Doppler technique. Also preferably, the velocity detecting means comprises a calculating means for calculating a Doppler shift signal from the echo by frequency analysis and calculating at every sample point an absolute velocity directed along a motion direction of the tissue.

It is preferred that the motion state analyzing means comprises a map displaying means for displaying a two-dimensional velocity-mapping image using the two-dimensionally mapped data of the velocity, a setting means for setting the plurality of local regions on the displayed two-dimensional velocity-mapping image, a calculating means for calculating velocity information in connection with each of the plurality of set local regions, and a further calculating means for calculating an index to the motion state of the tissue using the calculated velocity information. The velocity information calculating means is a means that averages a plurality of velocity data into a typical velocity, the plurality of velocity data consisting of data falling into each of local regions on the two-dimensional velocity-mapping image. For example, the tissue is either one of a cardiac muscle or a vascular wall of the object. The plurality of local regions set by the setting means are two regions of interest (ROIs) separately set on either one of the cardiac muscle or the vascular wall. The setting means is a means that separately sets the two ROIs on an endocardium and epicardium of the cardiac muscle. It is preferred that the index is at least one of a velocity difference between the typical velocities of the two ROIs, a velocity ratio between the typical velocities of the two ROIs, and a velocity gradient between the typical velocities of the two ROIs.

Accordingly, velocities of motions made by a tissue (for example, the cardiac muscle or vascular wall) that act to produce motion in a living body are detected, and used to create a velocity distribution on a section containing the tissue. The motion state of the tissue is analyzed on the basis of velocities associated with a plurality of local regions (for example, regions defined with two ROIs) in the velocity distribution. Analysis data includes a difference in velocity between local regions, a ratio of the velocity of one local region to that of the other region, and a velocity gradient. The analysis data is displayed on a monitor or the like. According to another aspect of the present invention, a diagnostic ultrasound system, comprising: means for detecting in real time a velocity of motion of a tissue contained in an object at every sampling point on a section of the object; means for creating time-sequentially a plurality of two-dimensionally mapped data of the velocities on the section; means for analyzing a motion state of the tissue on the basis of local velocities falling into a plurality of local regions set on each of the plurality of two-dimensionally mapped data of the velocities; means for forming time-dependent velocity data according to results analyzed by the motion state analyzing means; and means for displaying the time-dependent velocity data.

According to still another aspect of the present invention, a diagnostic ultrasound system, comprising: means for detecting a velocity of motion of a tissue contained in an object at every sampling point in a section of the object; means for creating two-dimensionally mapped data of the velocities in the section; means for calculating a velocity gradient on the two-dimensionally mapped data of the velocity; and means for displaying the velocity gradient as a two-dimensional image.

As still another aspect of the present invention, there is provided a method of imaging in ultrasound diagnosis, the method comprising the steps of: detecting a velocity of motion of a tissue contained in an object at every sampling point in a section of the object; creating two-dimensionally mapped data of the velocity in the section; analyzing a motion state of the tissue on the basis of local velocities falling into a plurality of local regions set on the two-dimensionally mapped data of the velocities; and displaying analysis results of the motion state.

BRIEF DESCRIPTION OF THE DRAWINGS

In the accompanying drawings:

FIG. 32A is an explanatory diagram showing setting of microscopic sections on segments along motion directions for obtaining velocity gradients; and FIG. 32B is a graph showing velocity profiles and their regression lines in every microscopic sections.

DETAILED DESCRIPTION OF THE PREFERRED EMBODIMENTS

First Embodiment

The first embodiment of the present invention will be described in conjunction with FIGS. 1 to 8. A diagnostic ultrasound system in accordance with this embodiment produces an image of the cardiac muscle or a vascular wall, which is a tissue, by performing tissue Doppler imaging (TDI).

Figure 1:
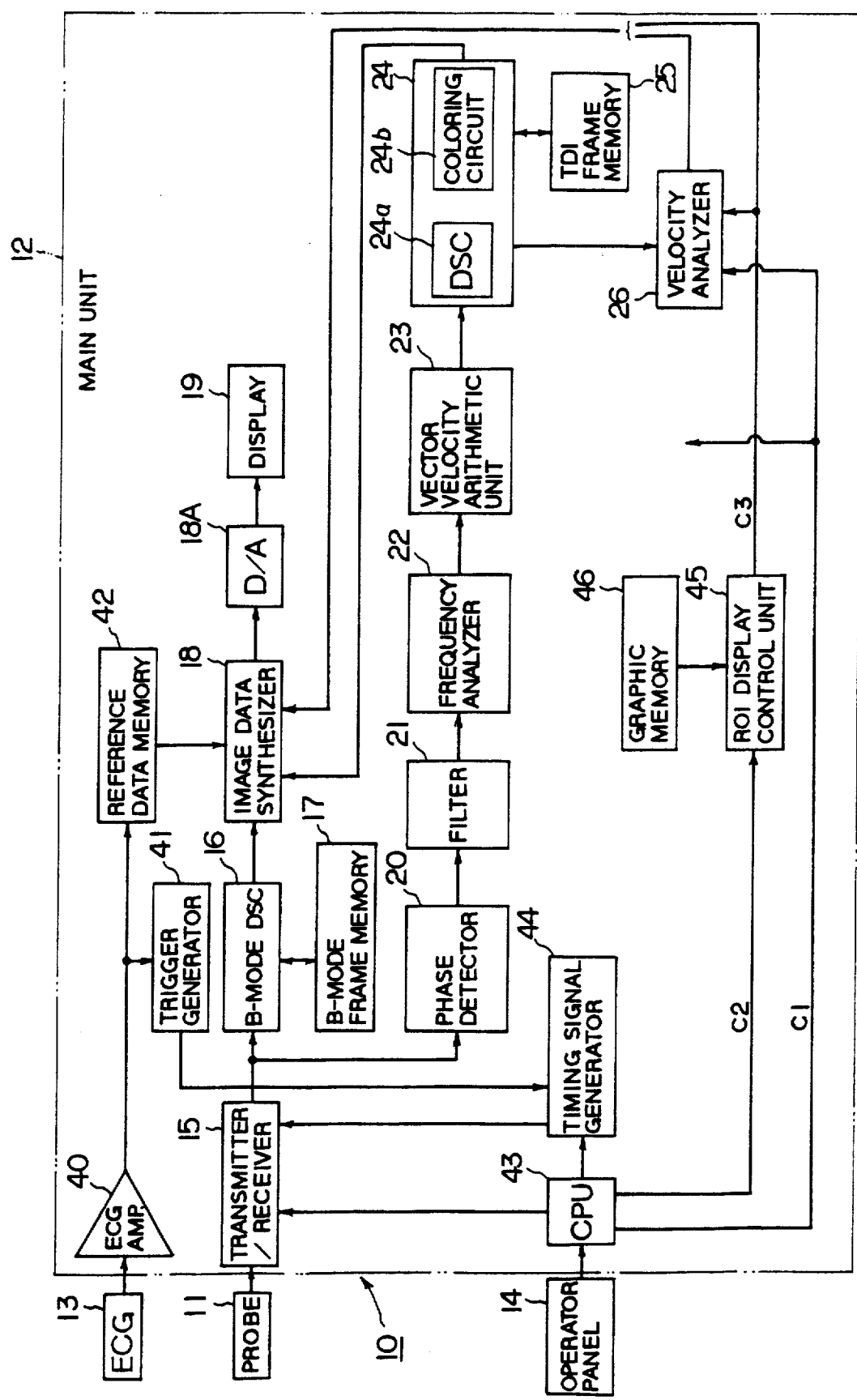
FIG. 1 is a block diagram showing a diagnostic ultrasound system in accordance with the first and sixth to eighth embodiments of the present invention.
Figure 2:
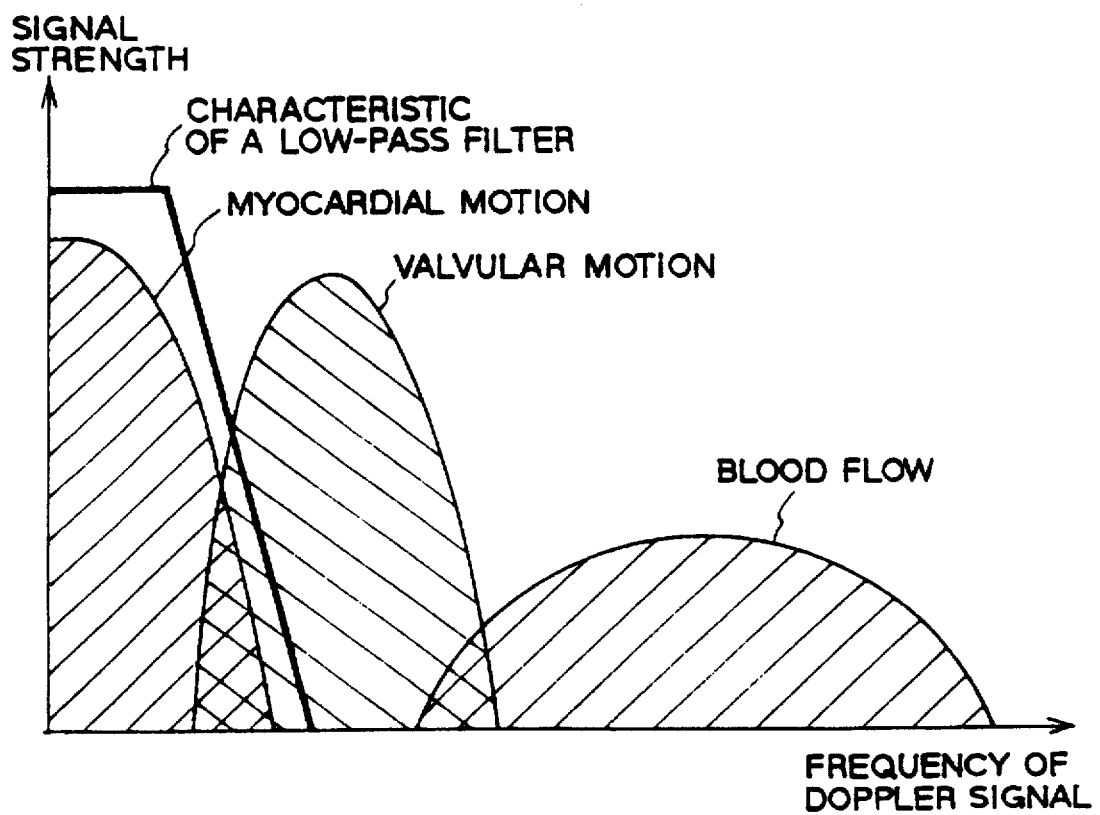
FIG. 2 is a graph showing a characteristic of a filter.

FIG. 1 is a block diagram showing the diagnostic ultrasound system. As illustrated, the diagnostic ultrasound system 10 comprises an ultrasound probe 11 for transmitting or receiving ultrasonic waves to or from a patient, a main unit 12 for driving the ultrasound probe 11 and processing signals received by the ultrasound probe 11, an electrocardiograph 13 (hereinafter ECG) connected to the main unit 12 and designed to detect electrocardiographic information, and an operator panel 14 connected to the main unit 12 and capable of outputting an instruction entered by an operator to the main unit.

The main unit 12 is broadly divided into an ultrasound probe system, an ECG system, and an operator panel system which handle different kinds of signals. The ultrasound probe system includes an ultrasonic-wave transmitter/receiver 15 connected to the ultrasound probe 11. Connected in the output stage of the ultrasonic-wave transmitter/receiver 15 are a B-mode digital scan converter (hereinafter B-mode DSC) 16, B-mode frame memory (FM) 17, an image data synthesizer 18, a D/A converter 18A, and a display 19. For tissue Doppler imaging based on pulsed Doppler imaging, the ultrasound probe system further includes a phase detector 20, a filter 21, a frequency analyzer 22, a vector velocity arithmetic unit 23, a DSC 24 designed for tissue Doppler imaging which will be referred to as a TDI DSC 24, a frame memory 25 designed for tissue Doppler imaging which will be referred to as a TDI frame memory 25, and a velocity analyzer 26. The ECG system includes an ECG amplifier 40 connected to the ECG 13. A trigger generator 41 and a reference data memory 42 are connected in the output stage of the amplifier 40. The operator panel system includes a central processing unit (hereinafter CPU)43 for inputting operational information entered at the operator panel 14, a timing signal generator 44 controlled by the CPU 43, a ROI display control unit 45, and a graphic memory 46. The CPU 43 can supply a ROI setting signal that finalizes a region of interest defined by an operator at the operator panel 14.

The ultrasound probe 11 has a phased-array transducer in which a plurality of strip-like piezoelectric elements are set in array. Each of the piezoelectric elements is excited with a driving signal sent from the ultrasonic-wave transmitter/receiver 15. Scan directions are changed by controlling the delay times of driving signals, whereby electronic sector scanning is achieved. A delay time pattern to be set in the ultrasonic-wave transmitter/receiver 15 is controlled by the CPU 43 with respect to a reference time instant indicated with a reference signal sent from the timing signal generator 44. The ultrasonic-wave transmitter/receiver 15 provides the ultrasound probe 11 with driving signals whose delay times are controlled depending on a scan direction. The transducers in the ultrasound probe 11 convert the driving signals into ultrasonic waves. The ultrasonic waves are delivered to the patient's heart. The delivered ultrasonic waves are reflected by the tissues including the heart and returned to the ultrasonic probe 11. The transducers in the probe 11 convert the reflected ultrasonic waves into voltages (electric echoes). The echoes are supplied to the ultrasonic-wave transmitter/receiver 15.

A signal processor in the ultrasonic-wave transmitter/receiver 15 delays the echoes and adds them for beam forming. Consequently, an echo beam equivalent to an electric ultrasound beam oriented in a scan direction is produced. When detected, the echo beam is supplied to the B-mode DSC 16. The DSC 16 converts the echo data resulting from ultrasonic scanning into data conformable to standard TV scanning, and then supplies the resultant data into the image data synthesizer 18. Meanwhile, the B-mode DSC 16 stores data representing a plurality of images produced at any cardiac time phase in the B-mode frame memory 17.

Echoes processed by the ultrasonic-wave transmitter/receiver 15 are also supplied to the phase detector 20. The phase detector 20 includes a mixer and a low-pass filter. Echoes emanating from a moving tissue such as the cardiac muscle or the like undergo a Doppler shift because of a Doppler effect. The phase detector 20 performs phase detection on the Doppler signals and provides the filter 21 with only those Doppler signals having low frequencies.

Based on the relationships that the velocities of myocardial motions are larger than those of valvular motions and the velocities of valvular motions are larger than those of blood flows (See FIG. 2), the filter 21 removes unnecessary Doppler signals induced by valvular motions and blood flows except myocardial motions from the Doppler signals that have undergone phase detection, and efficiently detects the Doppler signal representing the cardiac muscle moving along an ultrasonic beam. In this case, the filter 21 functions as a low-pass filter.

The filter is incorporated in a color Doppler tomography system that has already been put on the market and is designed to provide blood flow information. As far as the color Doppler tomography system for providing blood flow information is concerned, the filter functions as a high-pass filter that handles echoes including Doppler signals induced by a blood flow, cardiac wall motion, and valvular motion alike, and removes all the Doppler signals except those representing the blood flows. When the filter is designed to selectively serve as a low-pass filter and a high-pass filter according to a diagnostic purpose of the system, the filter can offer excellent versatility.

The strength of a signal returned from the cardiac muscle is very high, while the strength of a signal returned from a blood flow is negligible. For tissue Doppler imaging, the system configuration without the filter 21 is conceivable. The system configuration will not cause any inconvenience in practice.

A Doppler signal passed by the filter 21 is supplied to the frequency analyzer 22 in the next stage. The frequency analyzer 22 operates on the basis of fast Fourier transform (FFT) or auto-correlation that is a technique of analyzing frequencies used for blood flow measurements in ultrasound Doppler imaging. The frequency analyzer 22 computes an average velocity and maximum velocity within a viewing time interval (time window) for each of sample points and provides them as velocity data. Specifically, an average frequency of Doppler signals representing scanned points (an average of velocities of motions made at the points to be viewed) and a variance (a disturbance in the spectrum of the Doppler signals) are computed in real time using FFT or auto-correlation. A maximum frequency of the Doppler signals (a maximum of velocities of motions made at the points to be viewed) is computed in real time using FFT. The results of analyzing the frequencies of the Doppler signals are supplied as color Doppler information concerning motion velocities to the vector velocity arithmetic unit 23 in the next stage.

Figure 3:
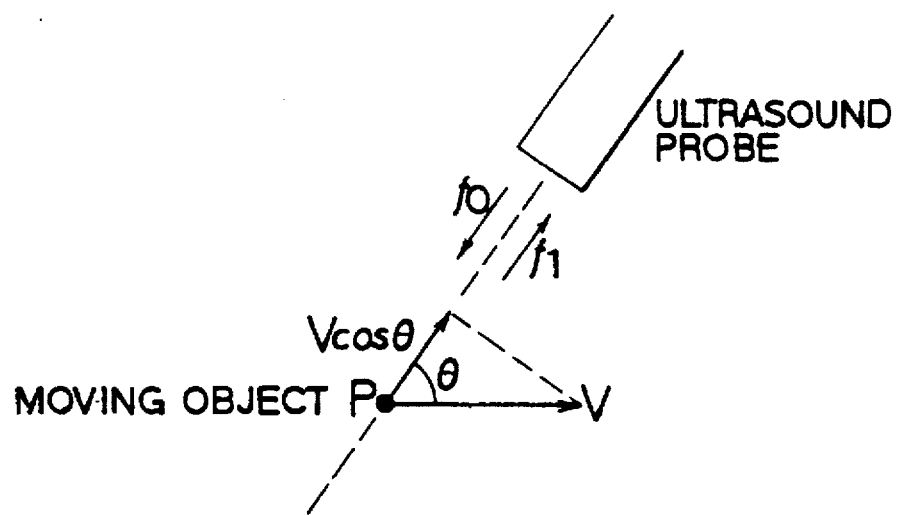
FIG. 3 is an explanatory diagram concerning scanning in pulsed Doppler mode.

The vector velocity arithmetic unit 23 estimates an absolute velocity of a motion made by a tissue such as the cardiac muscle (as shown in FIG. 3, a vector whose direction corresponds to the motion direction of an object P and whose magnitude corresponds to the velocity V of each motion) using, for example, the technique described in Japanese Patent Laid-Open No. 6-114059.

The vector velocity arithmetic unit 23 can calculate the absolute velocity using various manners. One of them is as follows.

Figure 4:
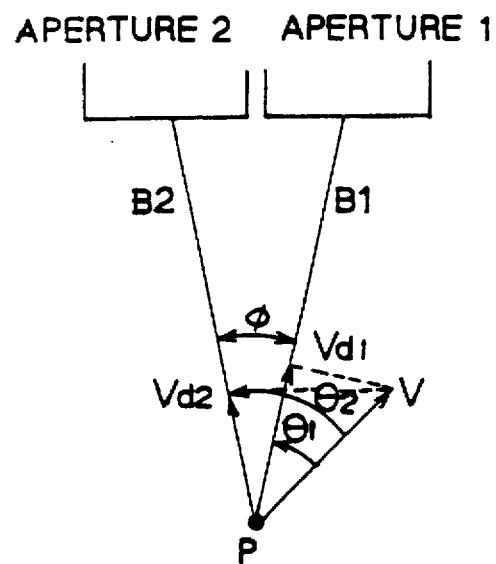
FIG. 4 is an explanation for measurement of an absolute velocity.

In FIG. 4, if the absolute velocity V of a moving object is assumed, components of velocities Vd1 and Vd2 in ultrasonic beam directions which can be estimated on Doppler shift frequencies obtained by two apertures 1 and 2, can be written as below.

$$Vd1 = V \times \cos \theta 1$$

$$Vd2 = V \times \cos \theta 2$$

Figure 5:
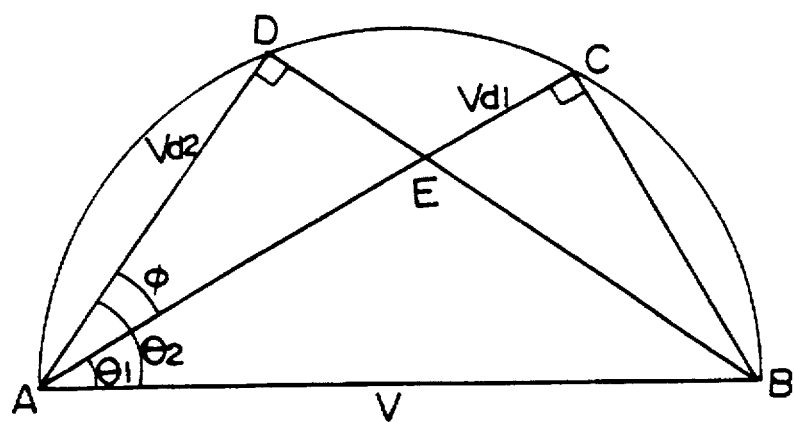
FIG. 5 shows a principle for calculating the absolute velocity.

These relations can be geometrically shown in FIG. 5, in which line segment AB=V line segment AC=Vd1=V×cos θ1 line segment AD=Vd2=V×cos θ2 is given. As the triangle ΔADE and the triangle ΔBCE are analogous to each other, line segment BC:line segment CE= line segment AD:line segment DE angle CBE=angle DAE=Ø are established. Also as line segment AD=Vd2 line segment DE=Vd2×tan Ø line segment CE=Vd1−Vd2/cos Ø, the equation $$\text{line segment } BC = \text{line segment } CE/\tan \emptyset$$
$$= (Vd1 - Vd2/\cos \emptyset)/\tan \emptyset$$
$$= Vd1 \times \cot \emptyset - Vd2/\sin \emptyset$$

is given. Therefore, the line segment AB, that is, the magnitude of the absolute velocity V is given as below.

$$V = \{(\text{line seg. } AC)^2 + (\text{line seg. } BC)^2\}^{1/2} \quad (1)$$
$$= \{Vd1^2 + (Vd1 \times \cot \emptyset - Vd2/\sin \emptyset)^2\}^{1/2}$$
$$= Vd1 \times \{1 + (\cot \emptyset - (Vd2/Vd1)/\sin \emptyset)^2\}^{1/2}$$

As seen from the equation (1), if an angle Ø between the two ultrasonic beams from the two apertures 1 and 2 is known, the absolute velocity V can be determined using the two Doppler shift outputs, with no relation to their incidence angles.

When the magnitude of the absolute velocity V is determined from the expression (1), using a relation of $$Vd1 = V \times \cos \theta 1$$

gives $$\theta 1 = \cos^{-1}(Vd1/V), \quad (2)$$

thus the direction of the absolute velocity V being determined.

In order to calculate an absolute velocity V according to the above theory, the transmitter/receiver 15 is constructed such that it controls delay time patterns and apertures in transmission and reception of the two ultrasonic beams. In response to this, the Doppler shift outputs Vd1 and Vd2, which correspond to the two ultrasonic beams B1 and B2, are supplied alternately from the frequency analyzer 22 to the vector velocity arithmetic unit 23, where the above expressions (1) and (2) are calculated.

The TDI DSC 24 includes a DSC 24a for changing scan modes, and a coloring circuit 24b having a look-up table for use in transforming velocity data into color data. Velocity data sent from the vector velocity arithmetic unit 23 is converted from the ultrasonic scan mode to the standard TV scan mode and transformed into color display data by the coloring circuit 24b and then fed to the image data synthesizer 18. The coloring circuit 24b produces color display data so that the systolic motion of the cardiac muscle and the diastolic motion thereof will be displayed in red (yellow) and blue (light blue) respectively in conformity with the conventional method in which the motion approaching an ultrasound beam and the motion receding therefrom are displayed in red and blue respectively. In addition, with an increase in velocity magnitude, the gradation of red or blue is changed into that of yellow or light blue.

The DSC 24a in the TDI DSC 24 places a plurality of images produced by performing tissue Doppler imaging, which shall be referred to as tissue Doppler images, at any cardiac time phase in the TDI frame memory 25 so that the images can be used for freezing.

The velocity analyzer 26 is connected in parallel with the TDI DSC 24 and interposed between the vector velocity arithmetic unit 23 and image data synthesizer 18. The velocity analyzer 26 inputs absolute velocity data representing vector velocities at two-dimensionally mapped sample points from the vector velocity arithmetic unit 23. The velocity analyzer 26 plays a pivotal role in the analysis of velocity data concerning a region of interest which relates to the gist of the present invention. In this embodiment, the velocity analyzer 26 includes a CPU and performs the sequence described in FIG. 7.

The ECG 13 detects electrocardiographic information at respective cardiac time phases of a patient, and places the information in the reference data memory 42. The reference data memory 42 stores the electrocardiographic information concerning cardiac time phases. Required information is supplied from the reference data memory 42 into the image data synthesizer 18 when it is needed. The trigger generator 41 informs the timing signal generator 44 of the timing of each cardiac time phase. The timing signal generator 44 operates under the control of the CPU 43 that controls a delay time pattern to be set in the ultrasonic-wave transmitter/receiver 15. When informed of the timing of each cardiac time phase by the trigger generator 41, the timing signal generator 44 delivers a reference signal used for transmission or reception of ultrasonic waves to the ultrasonic-wave transmitter/receiver.

As mentioned above, the image data synthesizer 18 receives a B-mode image signal from the B-mode DSC 16, an image signal representing an image, of which colors are mapped by performing tissue Doppler imaging, from the TDI DSC 24, two-dimensional velocity-mapping data from the velocity analyzer 26, and, if necessary, electrocardiographic information from the reference data memory 42. The image data synthesizer 18 synthesizes these input signals in superposition or division mode. The superposed data is supplied to the display 19. The display 19 is a CRT, for example.

In this embodiment, the ultrasound probe 11, ultrasonic-wave transmitter/receiver 15, phase detector 20, filter 21, frequency analyzer 22, and vector arithmetic unit 23 constitute a velocity detecting means of the present invention. The TDI DSC 24 and TDI frame memory 25 constitute a velocity distribution creating means of the present invention. The image data synthesizer 18, D/A converter 18A, and display 19 constitute a display means of the present invention. The operator panel 14, CPU 43, ROI display control unit 45, graphic memory 46, and velocity analyzer 26 constitute an analyzing means of the present invention.

Next, the operation of this embodiment will be described. Assuming that the cardiac muscle is evaluated, since Doppler signals induced by blood flows and valvular motions have already been cut off by the filter 21 (or such Doppler signals are negligible because of the low strengths), a tomographic image made by superposing a color Doppler image (for example, a short-axis image of the left ventricle), which renders myocardial motions with different colors, on a B-mode tomographic image (black-and-white gray scale) of the heart is displayed in read time as, for example, shown in FIG. 6 (the hatched part of FIG. 6 indicates the cardiac muscle HM). Specifically, the cardiac muscle HM in FIG. 6 appears in red (yellow) during systole and in blue (light blue) during diastole. The appearances in red and blue are repeated cyclically and in real time. In addition, a change in motion velocity during systole or diastole is expressed in real time as a change in tone of red (or yellow) or blue (or light blue). The velocities of motions made by the cardiac muscle HM can therefore be rendered substantially in real time with high precision. Thus, the image serves as a basis image essential for quantitative and high-precision assessment of hypofunction of the heart.

When a color Doppler image of the cardiac muscle is thus produced by tissue Doppler imaging, if a command C1 instructing velocity analysis is entered at the operator panel 14, the sequence described below is started.

In response to the velocity analysis command C1, the B-mode DSC 16 and TDI DSC 24 freeze an image appearing on the display 19.

Figure 7:
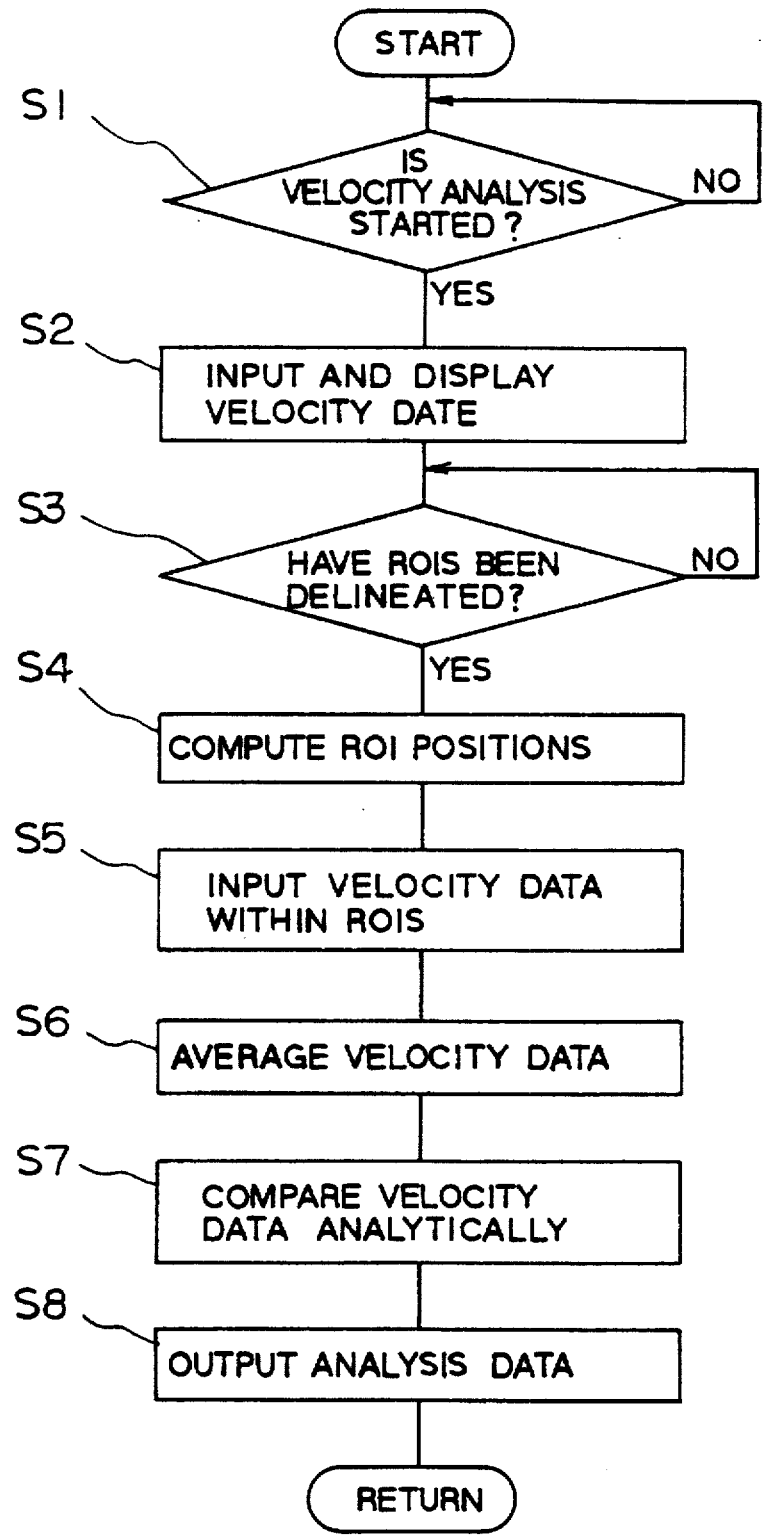
FIG. 7 is a simplified flowchart describing a sequence performed by a velocity analyzer in the first embodiment.

Meanwhile, the velocity analyzer 26 starts the sequence described in FIG. 7. Specifically, at step S1, the velocity analyzer 26 attempts to read the velocity analysis command C1 and determines whether manipulation of velocity data should be started. When the velocity analysis command C1 can be read in, the determination is made in the affirmative.

Control is then passed to step S2, and two-dimensional velocity-mapping data concerning one frame of the frozen image is received from the DSC 24a and displayed.

Figure 8:
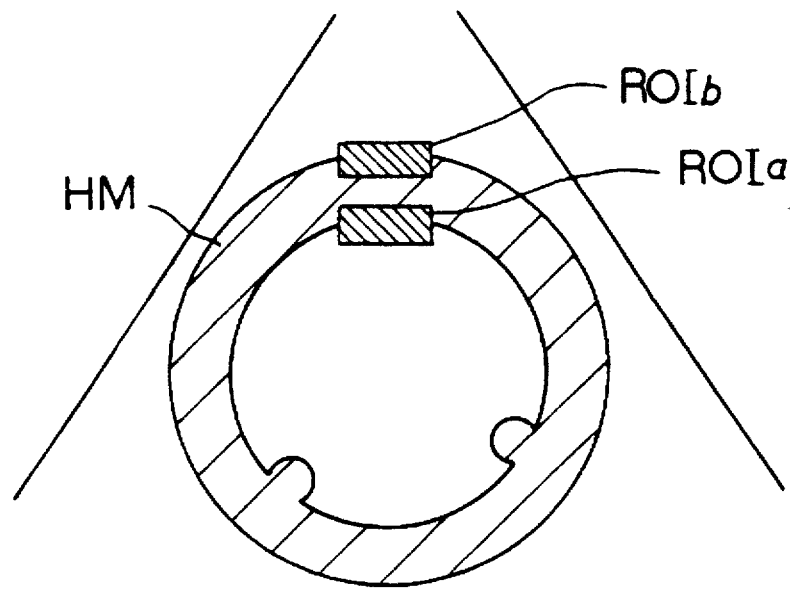
FIG. 8 is an explanatory diagram concerning two ROIs set in an image produced by tissue Doppler imaging in the first embodiment.

At step S3, the velocity analyzer 26 determines whether an operator has delineated a plurality (for example, two) of regions of interest or ROIs at desired positions in the frozen image appearing on the display 19. Assuming that the operator views the frozen image on the display 19 and enters at the operator panel 14 a command saying that the operator wants to manually delineate two rectangular ROIs at desired positions on an endocardium and epicardium because the ROIs positioned on the endocardium and epicardium are useful for diagnosis of a cardiac disorder, the CPU 43 issues a ROI setting signal C2 to the ROI display control unit 45. The ROI display control unit 45 interprets the ROI setting signal C2 so as to obtain required information including ROI shapes, the number of ROIs, and positions of displaying the ROIs. The ROI display control unit 45 reads graphic data concerning the designated ROI shapes from the graphic memory 46 and sends the ROI information C3 to the image data synthesizer 18. As a result, the designated number of ROIs having the designated shapes are displayed at the designated positions on the endocardium and epicardium in the frozen image. In this embodiment, as shown in FIG. 8, rectangular ROIs of ROIa and ROIb are displayed at the desired positions on the endocardium and epicardium.

At step S3 in FIG. 7, the velocity analyzer 26 attempts to read the ROI information C3 and at the same time determines whether ROIs have been delineated. The velocity analyzer 26 repeats the determination and stays in standby mode until the determination can be made in the affirmative (ROIs have been delineated).

When the determination can be made in the affirmative at step S3 (ROIs have been delineated), control is passed to step S4. The positions of areas (sets of pixels) defined with the two ROIs of ROIa and ROIb respectively are computed. Thereafter, the velocity analyzer 26 passes control to step S5 and receives two-dimensional velocity-mapping data associated with the pixels in the areas defined with the ROIs of ROIa and ROIb from the DSC 24a.

Since it is conceivable that velocity magnitude distribution varies according to positions within each of the ROIs of ROIa and ROIb, the input velocity data is averaged for each ROI in order to obtain typical velocities at step S6. As a result, a typical velocity $V_{end}$ is obtained relative to the ROI of ROIa set on the endocardium, and a typical velocity $V_{epi}$ is obtained relative to the ROI of ROIb set on the epicardium.

The velocity analyzer 26 passes control to step S7, and analytically compares the typical velocity $V_{end}$ with the typical velocity $V_{epi}$. Specifically, a difference in velocity between the endocardium and epicardium, $V_{DIFF}$, is calculated by subtracting the $V_{epi}$ value from the $V_{end}$ value ($V_{DIFF}=V_{end}-V_{epi}$), and a ratio of the velocity on the endocardium to the one on the epicardium, $V_{RATIO}$, is calculated by dividing the $V_{end}$ value by the $V_{epi}$ value ($V_{RATIO}=V_{end}/V_{epi}$). Alternatively, a gradient between the typical velocities $V_{end}$ and $V_{epi}$ may be calculated.

Thereafter, control is passed to step S8. The difference in velocity between the endocardium and epicardium, $V_{DIFF}$, and the ratio of the velocity on the endocardium to the one on the epicardium, $V_{RATIO}$, which are calculated at step S7, are supplied as analysis data to the image data synthesizer 18. As a result, the analysis data are displayed in the form of numerical values as part of a tomographic tissue Doppler image (color Doppler image), which is shown in FIG. 8.

Figure 6:
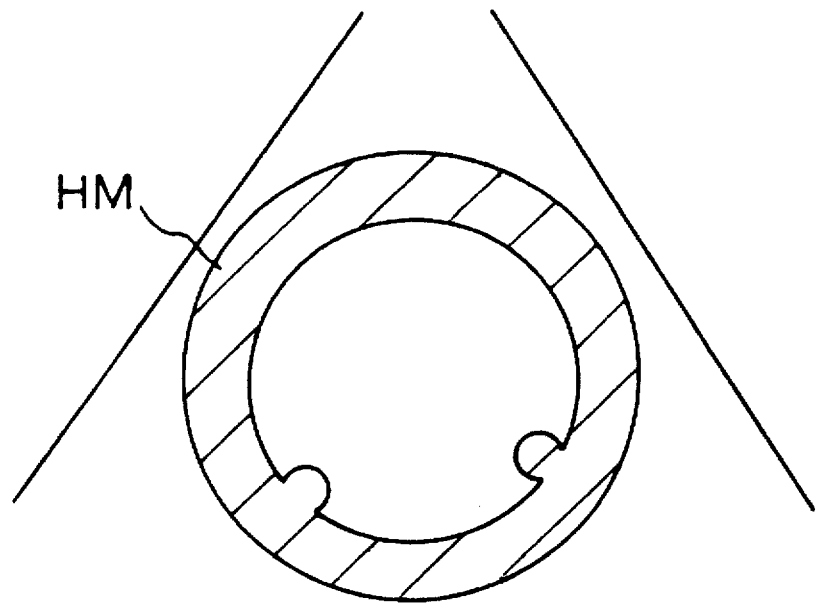
FIG. 6 shows an example of an image of the cardiac muscle produced by tissue Doppler imaging in the first embodiment.

A difference in velocity and a ratio of velocities between regions of interest (ROIa and ROIb) in the tomographic tissue Doppler image shown in FIG. 6 is displayed quantitatively. Consequently, not only the motion state of the cardiac muscle can be perceived from a whole image, but also the localized motion state of the cardiac muscle can be measured quantitatively. Even when there is another region of interest in the tomographic tissue Doppler image, an operator should only manually move the ROIs of ROIa and ROIb to the region. The results of analysis made by comparing data concerning the new ROIs are promptly displayed in the form of numerical values. As mentioned above, the motion state of a desired region in the cardiac muscle can be grasped accurately by moving the ROIs of ROIa and ROIb. An advantage unavailable when only the tomographic tissue Doppler image shown in FIG. 6 is displayed; that is, an advantage that localized hyposystole can be identified readily by comparing velocity differences (between an endocardium and epicardium) detected at different regions. This results in markedly improved diagnostic ability. Unlike stress echocardiography, the heart need not be stressed. The diagnostic ultrasound system therefore causes little patient discomfort or pain and thus proves a well-acceptable modality.

For providing the above advantage, ROIs are delineated at desired positions in a tomographic tissue Doppler image superposed on a B-mode image. The cardiac muscle need not be manually outlined with a B-mode image kept in view, but the contour of the cardiac muscle can be viewed and discerned readily. ROIs can therefore be set quickly and effortlessly. This is advantageous in terms of workability. The diagnostic ultrasound system can be utilized fully irrespective of operator's expertise.

In the first embodiment, pulsed Doppler imaging is used to compute velocities of myocardial motions. Alternatively, the velocities of myocardial motions may be computed using, for example, B-mode image data. Specifically, cross-correlation or any other technique is used to time-sequentially match patterns with a portion of B-mode image data representing a tissue, so that the velocities of motions made by the tissue are computed. In this case, the velocity analyzer 26 uses the computed motion velocities to carry out the aforesaid sequence.

Figure 9:
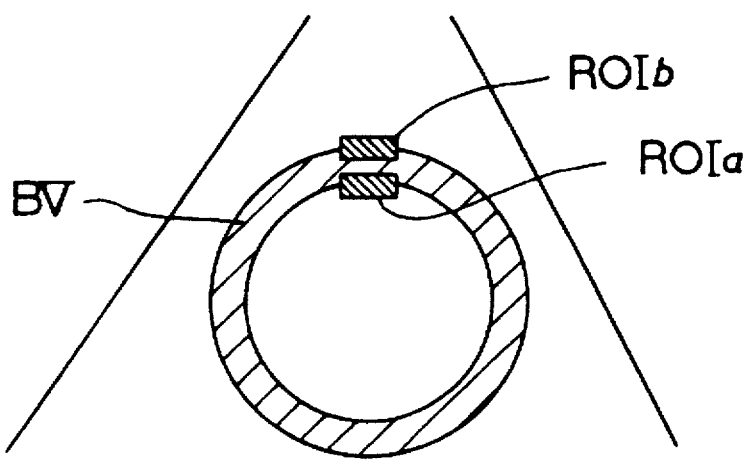
FIG. 9 is an explanatory diagram concerning two ROIs set in an image of a vascular wall produced by tissue Doppler imaging in a variant.

In the first embodiment, the motion state of a tissue that is the cardiac muscle is assessed. An object to be diagnosed may be vascular walls. FIG. 9 shows a tissue Doppler image of a vascular wall BV appearing on the display 19 in the diagnostic ultrasound system of the first embodiment. Two ROIs of ROIa and ROIb are set at desired positions on the tunica intima and tunica externa visualized in the tissue Doppler image. Average motion velocities $V_{in}$ and $V_{out}$ within the ROIs are calculated as typical velocities (See Steps S1 to S6 in FIG. 7). Based on the velocities $V_{in}$ and $V_{out}$, a difference in motion velocity between the tunica intima and tunica externa, $V_{DIFF}$, and a ratio of the motion velocity on the tunica intima to the one on the tunica externa, $V_{RATIO}$, are calculated as follows:

$$V_{DIFF}=V_{in}-V_{out}$$

$$V_{RATIO}=V_{in}/V_{out}$$

The calculated values are displayed (See Steps S7 and S8 in FIG. 7). Even when a vascular wall is to be evaluated, velocity data obtained at two positions can be compared analytically. Localized hypokinesia can be identified readily.

Second Embodiment

The second embodiment of the present invention will be described in conjunction with FIGS. 10 and 11. A diagnostic ultrasound system of the second embodiment is adaptable to tissues moving radially. ROIs specifying two regions required for analytic comparison of velocities can be set automatically.

Figure 10:
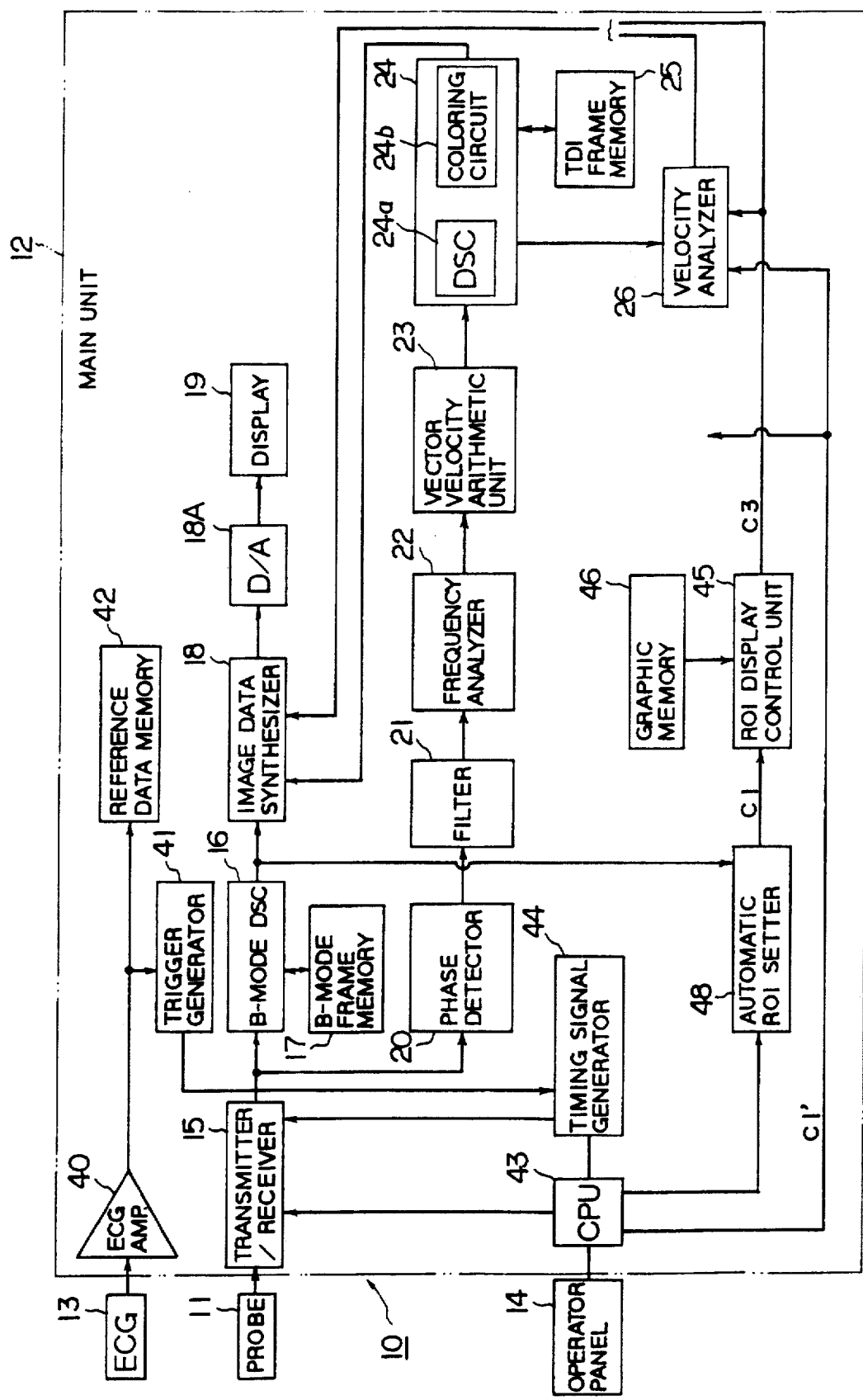
FIG. 10 is a block diagram showing a diagnostic ultrasound system in accordance with the second embodiment of the present invention.

A diagnostic ultrasound system shown in FIG. 10 has an automatic ROI setter 48 interposed between the CPU 43 and ROI display control unit 45 in addition to the components shown in FIG. 1. The automatic ROI setter 48 initiates the sequence shown in FIG. 11 in response to an automatic ROI setting command C1' sent from the CPU 43.

The sequence will be described in detail. The automatic ROI setter 48 inputs and displays B-mode image data concerning a frozen image at step S10 in FIG. 11. An image to be handled is a tomographic image of a tissue contracting and dilating substantially concentrically on a section. For example, an short-axis image of the parasternal left ventricle, which is an ultrasound tomographic image used most frequently for diagnosis of cardiac disorders, or a tomographic image of a vascular wall will do.

Control is then passed to step S11. The automatic ROI setter 48 specifies a contraction center in a B-mode image by manual or automatic operation. For manual operation, an operator enters point information at the operator panel 14 while viewing the frozen image on the display 19 and designates the point as a contraction center. For automatic operation, a center of an area or a vector oriented in a direction of contraction made by the cardiac muscle is computed in order to determine and specify a contraction center.

At step S12, an endocardium and epicardium are identified in one radial direction in the B-mode image with respect to the contraction center as a center. Contour extraction used for the identification is performed using a known technique (for example, refer to Japanese Patent Laid-Open No. 6-114059).

At step S13, position information C1 concerning the identified endocardium and epicardium is supplied to the ROI display control unit 45. As a result, the ROI display control unit 45 displays, for example, rectangular ROIs of ROIa and ROIb on the identified endocardium and epicardium on the basis of the position information C1 (See FIG. 8). Analytic comparison between the two-dimensional velocity-mapping data concerning the ROIs of ROIa and ROIb is carried out by the velocity analyzer 26 in the same manner as mentioned above.

Figure 11:
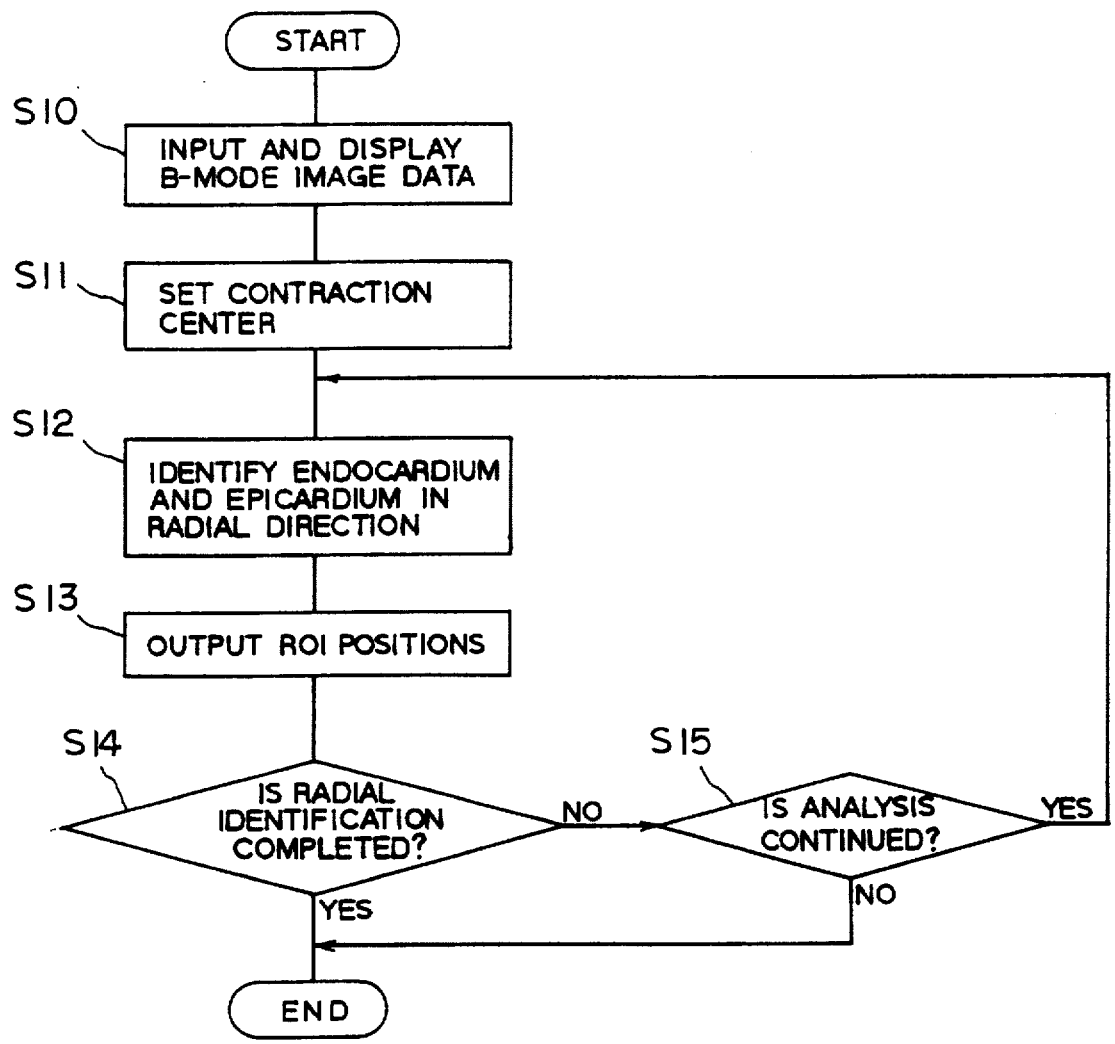
FIG. 11 is a simplified flowchart describing a sequence performed by an automatic ROI setter in the second embodiment.

Thereafter, the automatic ROI setter 48 determines whether radial scanning (that is, identification of the positions of the endocardium and epicardium) has been completed (step S14 in FIG. 11). If it has not been completed, the automatic ROI setter 48 determines on the basis of a command entered by the operator whether ROI setting should be continued (step S15 in FIG. 11). For continuing ROI setting, control is returned to step S12. The endocardium and epicardium are positionally identified in a radial direction with respect to another position around the contraction center (for example, a position in a radial direction adjoining the radial direction). Thus, positions of ROIs are determined automatically.

By repeating the foregoing sequence, ROIs of ROIa and ROIb are automatically and consecutively set at radial positions relative to the contraction center. Thus, operating work is saved drastically. A difference in motion velocity between the endocardium and epicardium located in the same direction is calculated through analytic comparison. A myocardial region necrosed due to myocardial infarction or the like can be evaluated readily and quantitatively.

Third Embodiment

The third embodiment of the present invention will be described in conjunction with FIGS. 12 to 15. In the third embodiment, analytic comparison of velocities measured within a plurality of regions is executed for a plurality of images time-sequentially in real time. Thus, a time-passing change in tissue motion is analyzed and displayed.

Figure 12:
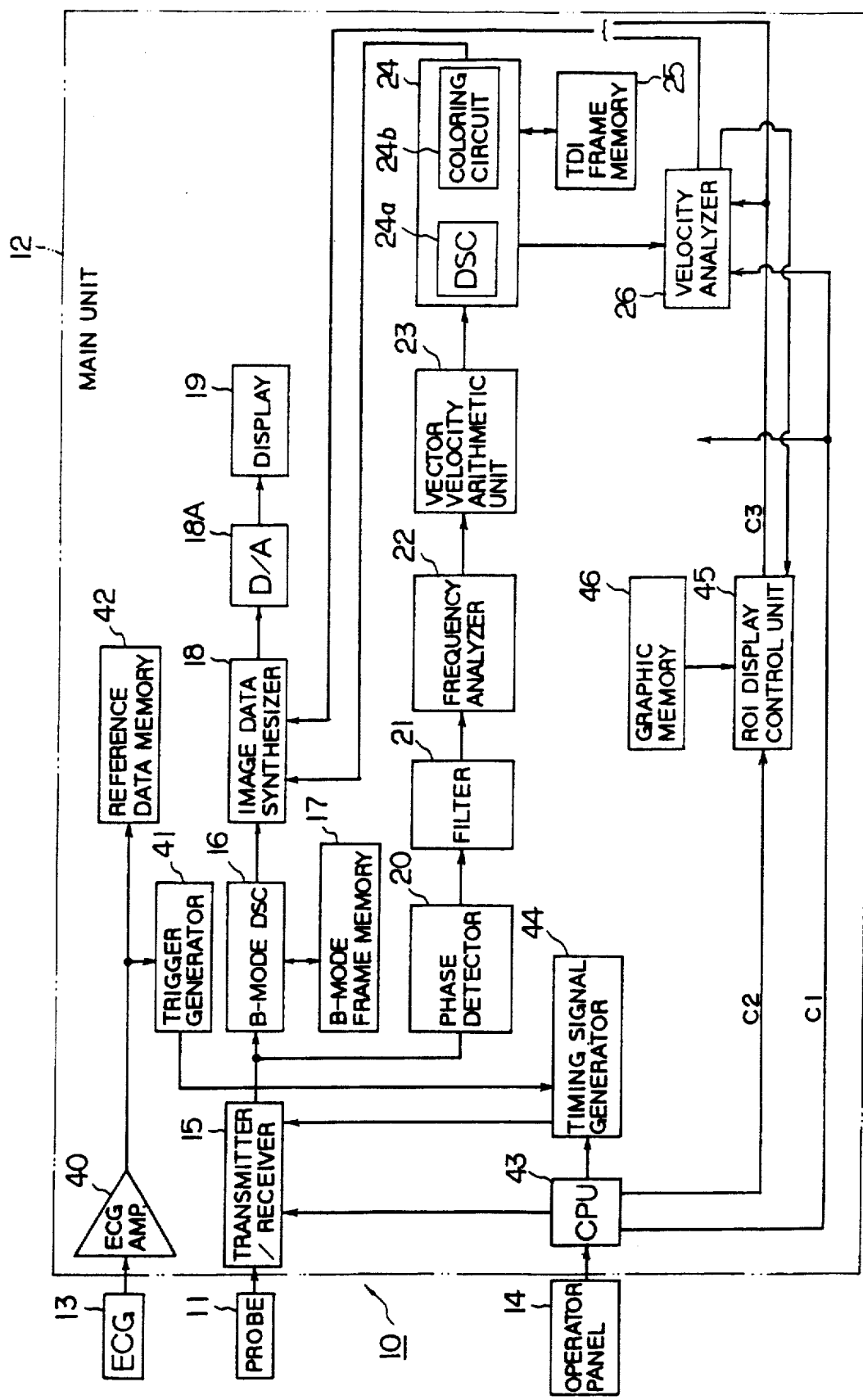
FIG. 12 is a block diagram showing a diagnostic ultrasound system in accordance with the third embodiment of the present invention.

For executing these operations, a diagnostic ultrasound system shown in FIG. 12 has the velocity analyzer 26 receiving image data representing a B-mode tomographic image. The velocity analyzer 26 performs ROI re-setting which will be described later, and supplies the results of ROI re-setting to the ROI display control unit 45.

Figure 13:
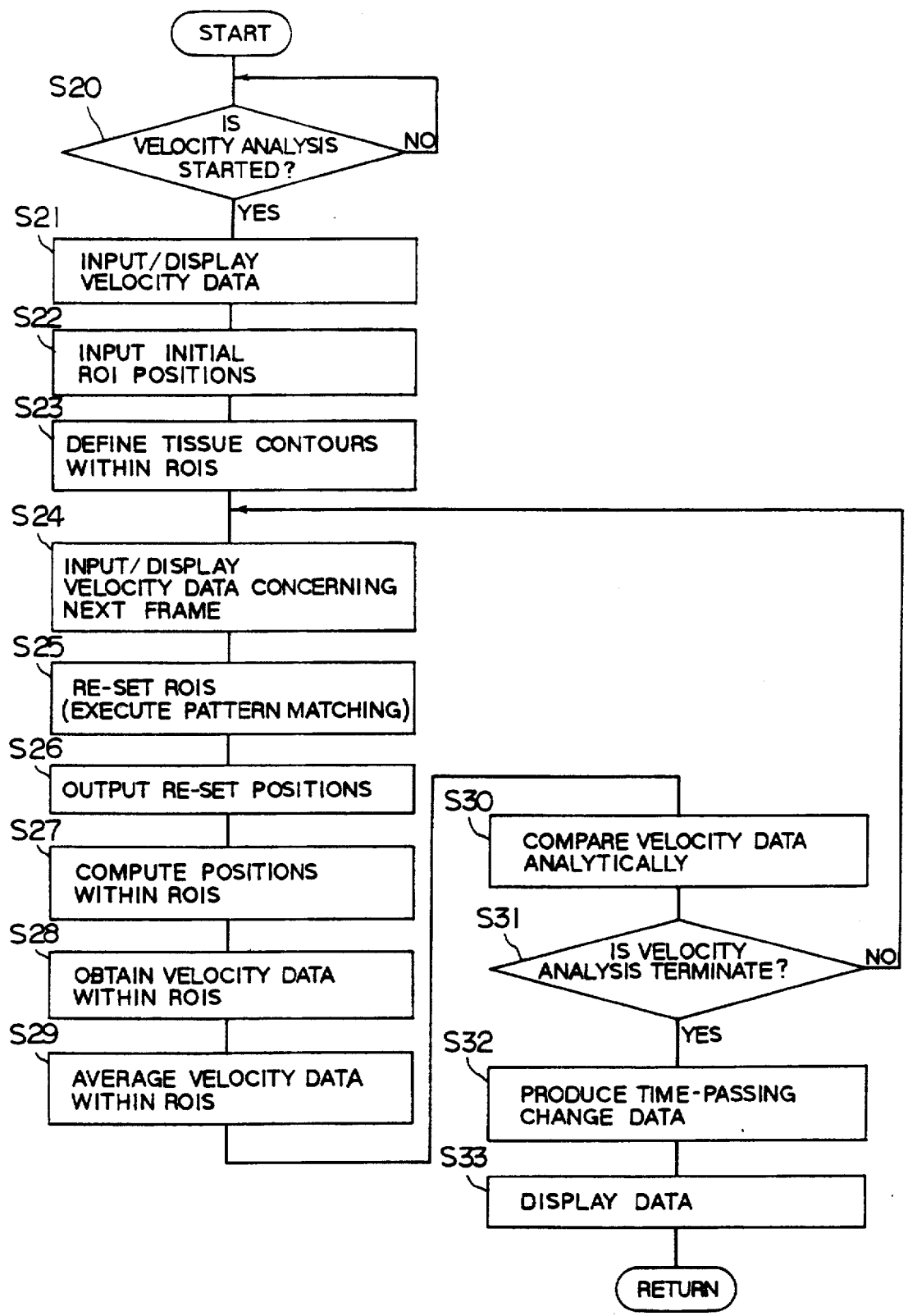
FIG. 13 is a simplified flowchart describing a sequence performed by a velocity analyzer in the third embodiment.
Figure 14:
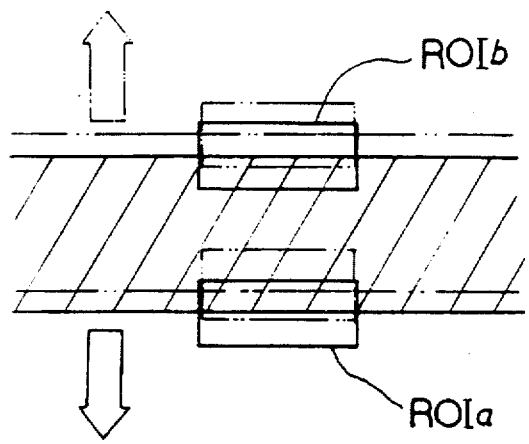
FIG. 14 is an explanatory diagram concerning automatic lock-on of ROIs relative to an endocardium and epicardium.

For the ROI re-setting, the velocity analyzer 26 carries out the sequence shown in FIG. 13. The sequence will be described below.

First, the velocity analyzer 26 determines on the basis of a command C3 sent via the ROI display control 45 whether velocity analysis is started (step S20 in FIG. 13). Steps S21 to S23 are then carried out sequentially. At step S21, two-dimensional velocity-mapping data at that time are input and displayed. At step S22, an operator enters the initial positions of ROIs of ROIa and ROIb through the ROI display control unit 45 at the operator panel 14 while viewing a B-mode frozen image appearing on the display 19. At step S23, contours of a tissue within the ROIs of ROIa and ROIb set at the initial positions are defined. That is, when the cardiac muscle is evaluated, the contours of the endocardium and epicardium are defined using a known technique.

After the contours of a tissue are thus defined, steps S24 to S26 are executed sequentially. At step S24, a set of velocity-mapping data rendering a next frame obtained in real time at that time is input and displayed. At step S25, the velocity-mapping image is matched with a pattern, and then the ROIs of ROIa and ROIb are automatically re-set. With the re-setting, the ROIs of ROIa and ROIb are automatically locked on to positions and/or contours of the tissue which vary with the passage of time (See the positions drawn with alternate long and two short dashed lines in FIG. 14). At step S26, the re-set position information is returned to the ROI display control unit 45. Thus, the ROIs of ROIa and ROIb that are automatically locked on to the tissue positions are superposed on a real-time velocity-mapping image subsequently displayed on the display 19.

Next, steps S27 to S30 are executed one after another. These steps are identical to steps S4 to S7 in FIG. 7. The velocity data concerning the two ROIs of ROIa and ROIb are compared mutually.

Figure 15:
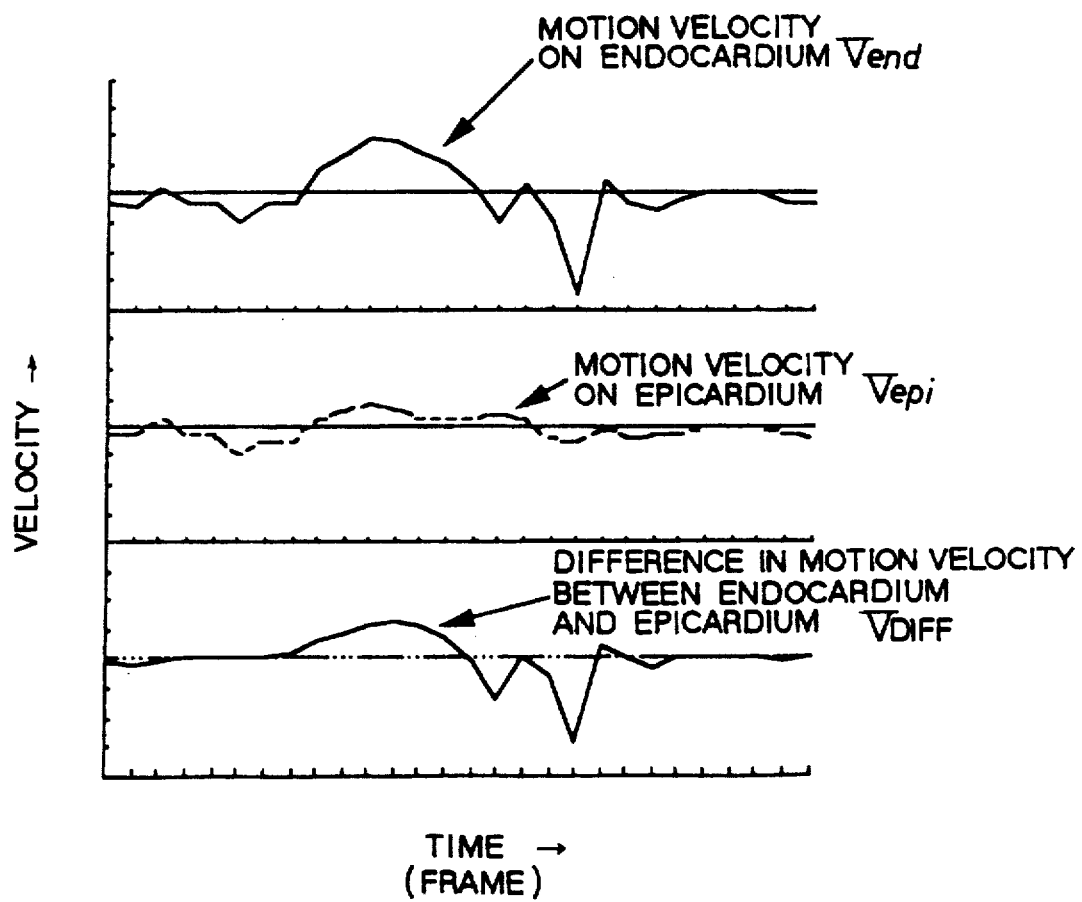
FIG. 15 shows a velocity change curve and velocity difference change curve displayed in the third embodiment.

Control is then passed to step S31. It is determined whether a command signal C1 issued by an operator should be received in order to terminate the sequence. If the determination is made in the negative, control is returned to step S24. The aforesaid sequence is repeated. If the determination is made in the affirmative, control is passed to step S32. Velocity data obtained by handling a plurality of frames at steps S29 and S30 are used to produce time-passing change data. Specifically, when the cardiac muscle is to be evaluated, data representing, for example, changes in motion velocity on an endocardium, in motion velocity on an epicardium, and difference in motion velocity between the endocardium and epicardium occurring with the passage of time (or with a change of frames) is produced. The produced data is supplied to the image data synthesizer 18 at step S33. Curves expressing changes in motion velocity on an endocardium, in motion velocity on an epicardium, and in difference in motion velocity between the endocardium and epicardium, which are plotted, for example, as shown in FIG. 15, with elapsed time indicated on the axis of abscissae, are displayed solely or superposed on another image.

As mentioned above, according to the third embodiment, two-dimensional velocity-mapping data within two ROIs can be compared analytically, and curves expressing time-passing changes in motion made by a tissue concerned can be displayed.

In the third embodiment, a plurality of B-mode frame data time-sequentially obtained can be used by the velocity analyzer 26 in order to perform pattern matching which produces two-dimensional velocity-mapping data for the foregoing time-sequential analysis.

Fourth Embodiment

The fourth embodiment of the present invention will be described in conjunction with FIGS. 16 to 19. The fourth embodiment is identical to the third embodiment in a point that analytic comparison of velocity data is performed time-sequentially in real time. However, the necessity of ROI lock-on (that is, contour definition or pattern matching) performed in the third embodiment is obviated.

Figure 16:
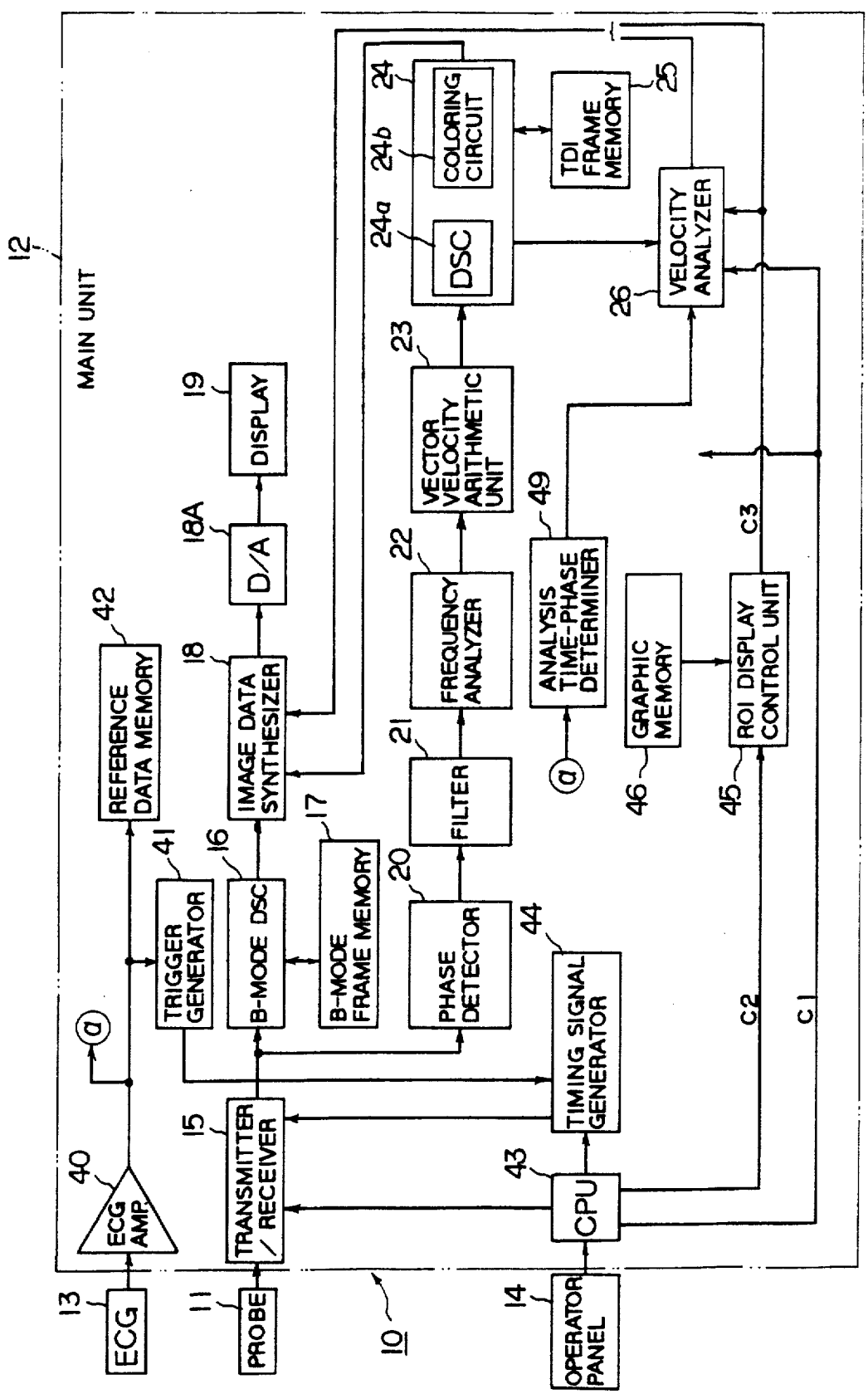
FIG. 16 is a block diagram showing a diagnostic ultrasound system in accordance with the fourth embodiment of the present invention.

Accordingly, a diagnostic ultrasound system shown in FIG. 16 includes an analysis time-phase determiner 49. The analysis time-phase determiner 49 receives an output signal of the ECG amplifier 40, determines a time phase, at which the motion velocity on an endocardium, $V_{end}$, becomes maximum, using, for example, a technique of threshold-based discrimination. The analysis time-phase determiner 49 then supplies the time phase information to the velocity analyzer 26. The other components are identical to those in FIG. 1.

Figure 17:
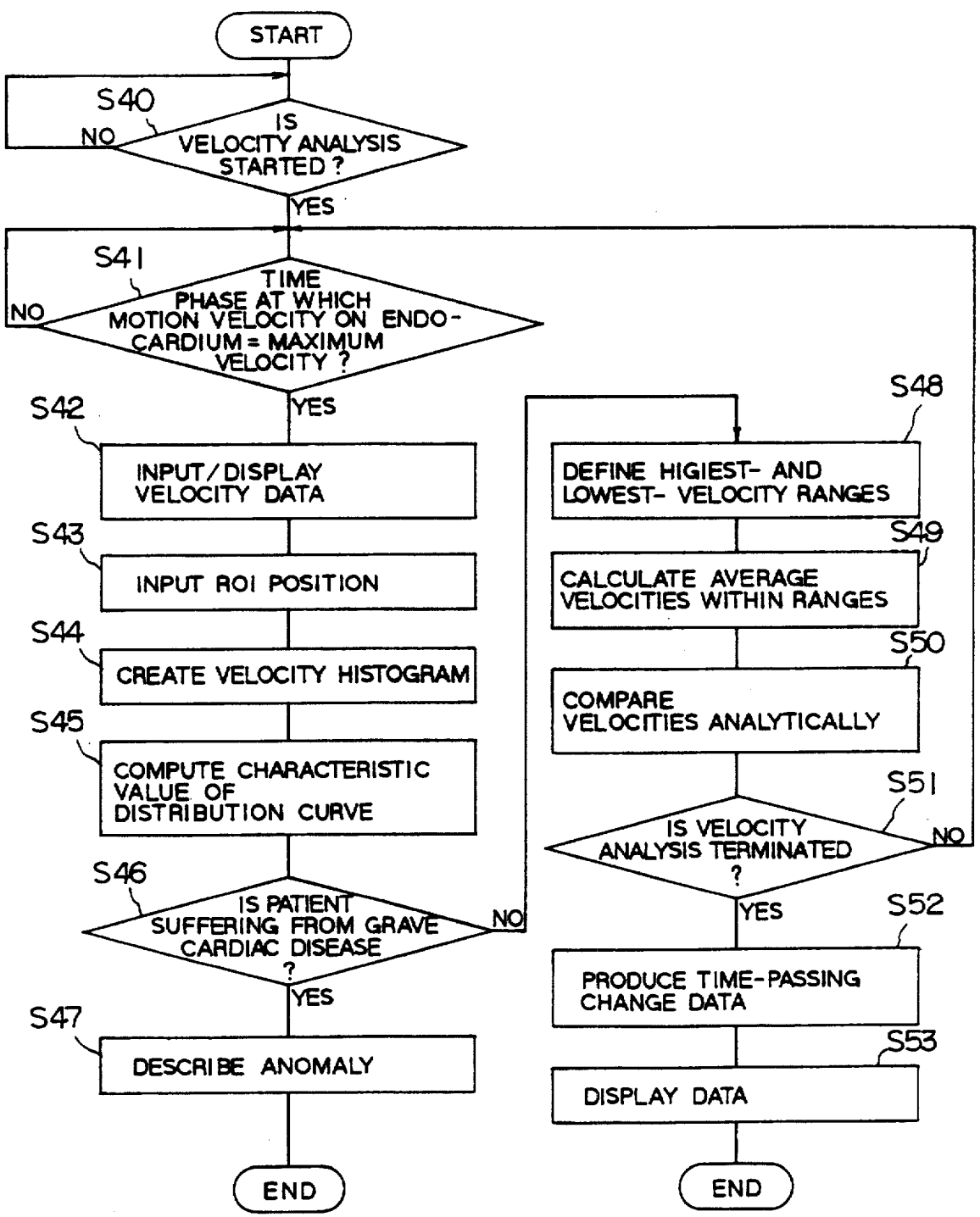
FIG. 17 shows a simplified flowchart describing a sequence performed by a velocity analyzer in the fourth embodiment.

The velocity analyzer 26 performs the sequence shown in FIG. 17. Specifically, when it is determined at step S40 that velocity analysis is started, control is passed to step S41. The velocity analyzer 26 reads time phase information sent from the analysis time-phase determiner 49 and determines whether it is the time phase at which the motion velocity on an endocardium equals to a maximum velocity. If it is determined that it is the time phase at which the motion velocity on an endocardium equals the maximum velocity, steps S42 to S46 are executed one after another.

Figure 18:
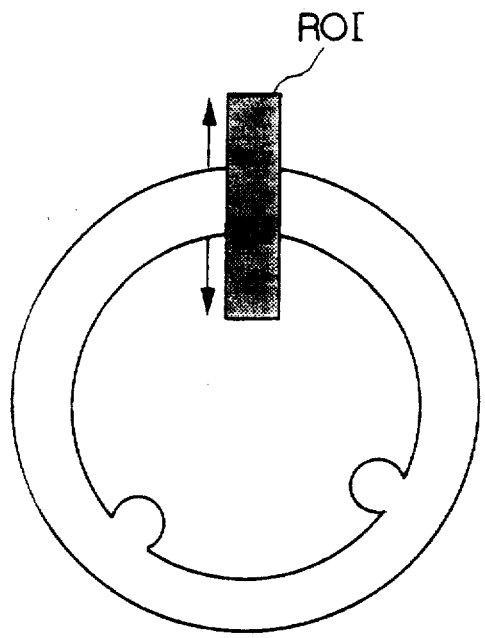
FIG. 18 shows a single ROI covering a range of myocardial motions.
Figure 19:
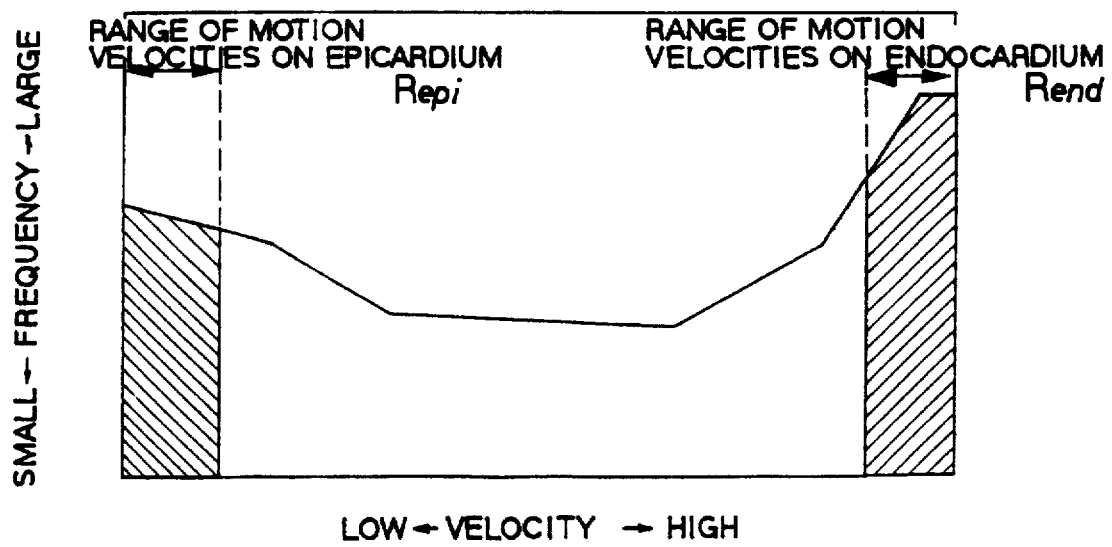
FIG. 19 shows a velocity histogram concerning a single ROI.

First, two-dimensional velocity-mapping data obtained at the time phase at which the motion velocity on an endocardium equals to the maximum velocity is received from the TDI DSC 24 and displayed (step S42). A designated ROI position is input through the ROI display control unit 45 (step S43). At this time, as shown in FIG. 18, one large rectangular ROI covering a maximum range of motions made by a tissue or the cardiac muscle is entered at the operator panel 14 by an operator.

Velocities measured within the designated ROI are used to create a histogram (step S44). Thus, data representing a frequency distribution curve that indicates frequencies of velocities as ordinates is stored in an incorporated memory.

Mention will be made of the necessity of creating the velocity histogram. In general, a displacement (distance moved) made by an endocardium during one cardiac cycle is larger than that made by an epicardium. In terms of velocities, the velocities of motions made by the endocardium, $V_{end}$, are much larger than those of motions made by the epicardium, $V_{epi}$. When a ROI covering a range of motions made by the endocardium and epicardium is specified as mentioned above, since the time phase at which the motion velocity on the endocardium becomes maximum is selected, a portion of the velocity histogram indicating the highest velocities measured on each section is regarded as a range of motion velocities on the endocardium, Rend, and a portion thereof indicating the lowest velocities is regarded as a range of motion velocities on the epicardium, Repi (See FIG. 19). Average velocities within the highest-velocity range Rend and lowest-velocity range Repi are comparable to averages of velocities measured within two ROIs spatially set on the endocardium and epicardium. This is the underlying idea of creating the velocity histogram in this embodiment.

However, as far as a patient suffering from grave wall-motion anomaly is concerned, the relationship that the motion velocities on an endocardium are higher than those on an epicardium is not always established. Measures must be taken to exclude this kind of case from velocity analysis.

At step S45, a characteristic value is computed that represents quantitative characteristics of a velocity histogram curve created at step S44. The characteristic value is, for example, a frequency of the highest velocity, a frequency of the lowest velocity, a difference in frequency between the highest and lowest velocities, an average frequency, or a difference between the average frequency and the frequency of the highest or lowest velocity. The characteristic value serves as an index for distinguishing a patient with a grave cardiac disease from other patients.

At step S46, the computed characteristic value of the frequency distribution curve is compared with a predetermined reference value in order to determine whether a patient suffers from a grave cardiac disease. If the patient is recognized as a patient with a grave cardiac disease, since the velocity analysis of the fourth embodiment will not be helpful, the anomaly (graveness) is described on the display 19 at step S47. The sequence is then terminated.

By contrast, if it is determined at step S46 that the patient is not a patient with a grave cardiac disease, steps S48 to S50 are executed consecutively. At step S48, certain ranges from the highest velocities and lowest velocities are defined as the range of motion velocities on an endocardium, Rend, and the range of motion velocities on the epicardium, Repi, respectively. At step S49, average velocities $V_{end}$ and $V_{epi}$ within the velocity ranges Rend and Repi are calculated as typical velocities. At step S50, the calculated average velocities Vend and Vepi are subjected to analytic comparison in the same manner as those in the aforesaid embodiments.

Thereafter, it is determined at step S51 whether the velocity analysis is terminated. If velocity analysis is continued, control is returned to step S41. The aforesaid sequence is repeated. For terminating velocity analysis, steps S52 and S53 (identical to steps S32 and S33 in FIG. 13) are executed.

The fourth embodiment provides the same results of velocity analysis as the third embodiment. Moreover, since one large ROI is specified and a velocity histogram is created, ROI lock-on; that is, contour defining of an endocardium and epicardium and pattern matching need not be executed. Nevertheless, the endocardium and epicardium can substantially be distinguished from each other. The sequence therefore includes a smaller number of operations.

Fifth Embodiment

The fifth embodiment will be described in conjunction with FIGS. 20 and 21. This embodiment relates to correction of a motion velocity measured on a tissue.

As described previously, the Doppler imaging technique of the present invention can, similarly to the conventional blood flow Doppler imaging technique, detect a velocity component of a motion oriented in a direction of scanning an ultrasound beam. When a vector velocity arithmetic unit is not incorporated in a diagnostic ultrasound system and the direction of a motion made by a tissue differs from the direction of scanning ultrasonic waves, correction must be made according to an angle between both the directions.

Figure 20:
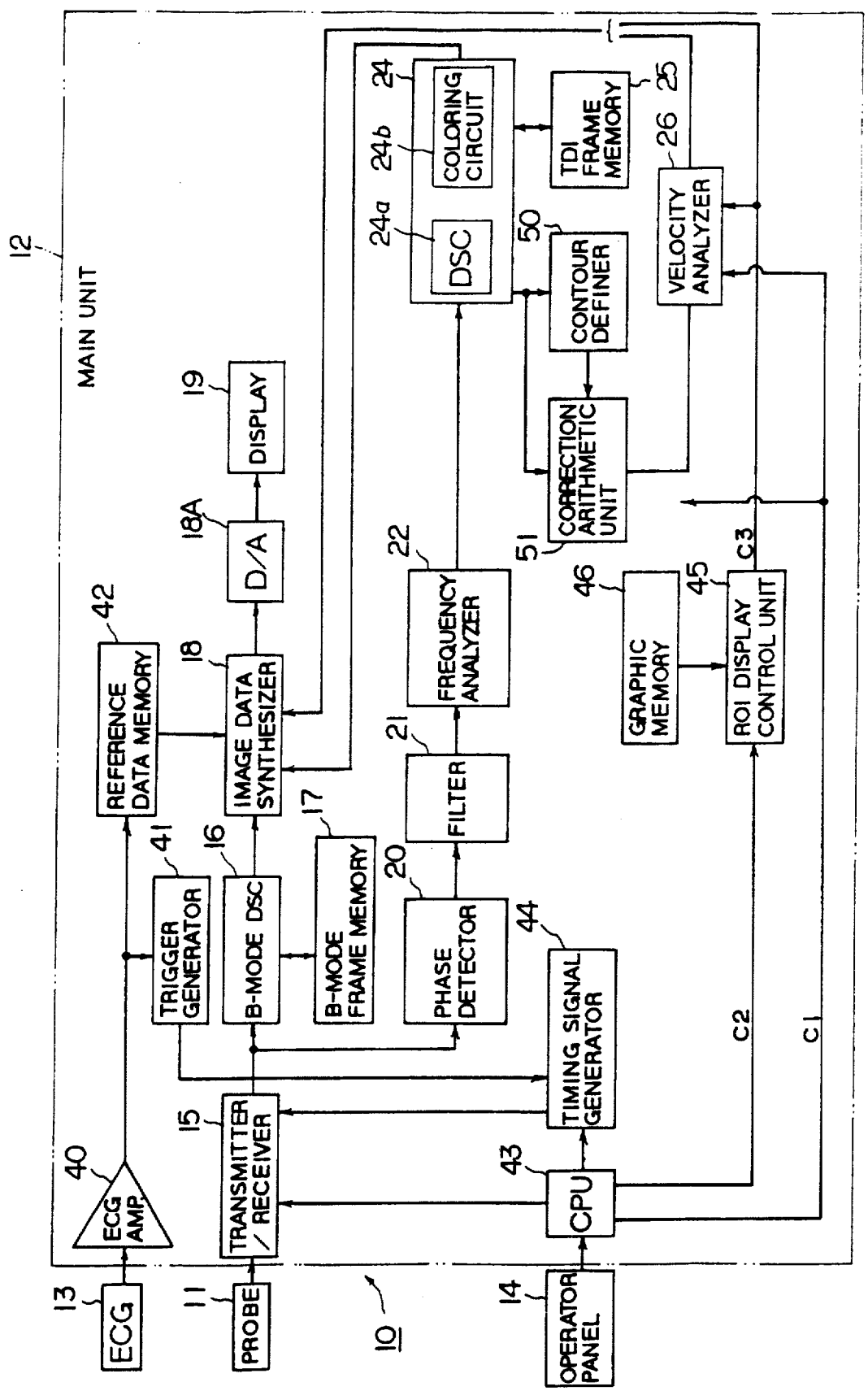
FIG. 20 is a block diagram showing a diagnostic ultrasound system in accordance with the fifth embodiment of the present invention.

In this embodiment, as shown in FIG. 20, an output of the frequency analyzer 22 is fed directly to the DSC 24. A contour definer 50 and a correction arithmetic unit 51 are added. The contour definer 50 uses two-dimensional velocity-mapping data supplied from the TDI DSC 24 to define the contours of an endocardium and epicardium of the cardiac muscle through cross-correlation, and then sends the contour information to the correction arithmetic unit 51. The correction arithmetic unit 51 corrects a detected velocity v provided by the frequency analyzer 22 for each of regions along the contour of the endocardium or epicardium.

Figure 21:
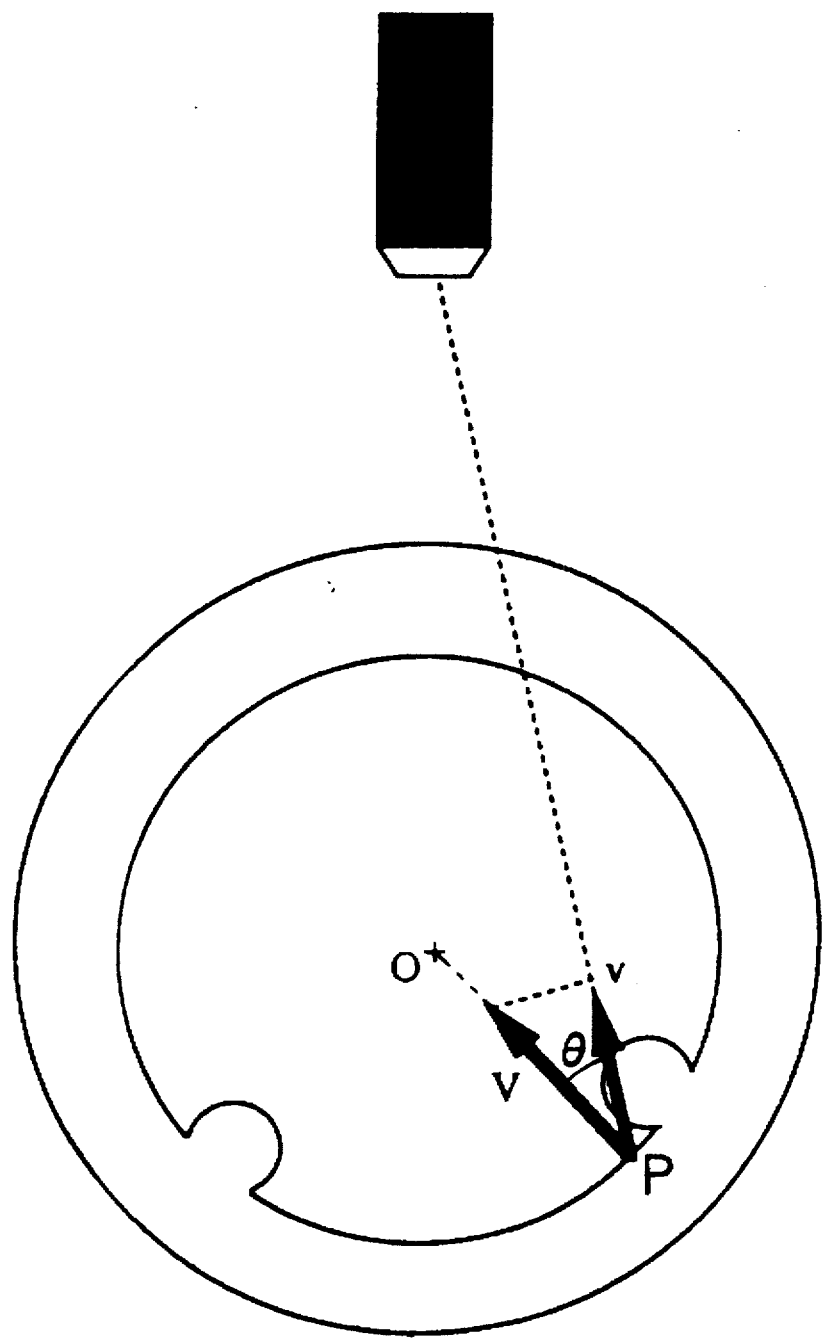
FIG. 21 is an explanatory diagram concerning Doppler angle correction.

FIG. 21 shows an example of an endocardium. A detected velocity component v and its direction (that is a direction of an ultrasound beam) are provided by the DSC 24. Assuming that an angle between a motion direction at a certain position P in the endocardium and the detected velocity component v is θ, a motion velocity V at the position P is calculated as follows:

$$V = v/\cos\theta$$

The angle θ is calculated by the correction arithmetic unit 51 on the assumption that each region of the cardiac muscle moves along a segment linking a certain position in the region and a contraction center O.

The correction arithmetic unit 51 executes the correction based on the above expression for the whole circumference of each of the endocardium and epicardium. Detected velocities v are corrected two-dimensionally in terms of angle, thus calculating absolute velocities V. Based on two-dimensionally mapped data representing the corrected velocities V, the velocity analyzer 26 carries out the velocity analysis in the same manner as mentioned previously.

Sixth Embodiment

The sixth embodiment will be described in conjunction with FIGS. 1, and 22 to 26. This embodiment calculates velocity gradients as results of analytic comparison and displays them in appropriate form.

A diagnostic ultrasound system of the sixth embodiment has the same configuration as the one shown in FIG. 1. The velocity analyzer 26 executes the sequence described in FIG. 22.

When velocity analysis is started at step S60, the velocity analyzer 26 receives two-dimensional velocity-mapping data concerning a section from the DSC 24 and displays them at step S61.

At step S62, position information concerning a contraction center of the cardiac muscle that is an object tissue, a contour of its endocardium, and a contour of its epicardium are produced automatically using the aforesaid known technique. Alternatively, an operator may enter the information manually while viewing a frozen image appearing on the display 19 (two-dimensional velocity-mapped image (tissue Doppler image)). An annular region defined with the endocardium and epicardium is specified as an object region relative to which velocity gradients are calculated in this embodiment.

At step S63, the velocity analyzer 26 acquires velocities within the specified region. For the acquisition, velocities are detected in a radial direction with respect to, for example, the contraction center of the cardiac muscle and stored in one-to-one correspondence to positions in the radial direction. For improved efficiency, the acquisition will not be carried out outside the object region.

Figure 23:
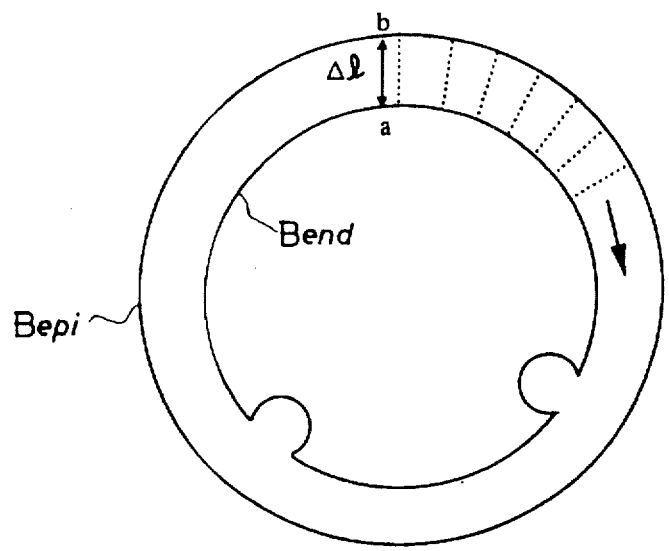
FIG. 23 is an explanatory diagram showing segments linking an endocardium and epicardium and being used to calculate a velocity gradient.

In another example of the acquisition made at step S63, as shown in FIG. 23, a plurality of segments corresponding to the shortest distance between an endocardium $B_{end}$ and an epicardium $B_{epi}$ are all drawn in the boundary of an object myocardial region visualized in a short-axis image of the parasternal left ventricle. Velocities are then detected on each of the segments.

Figure 24:
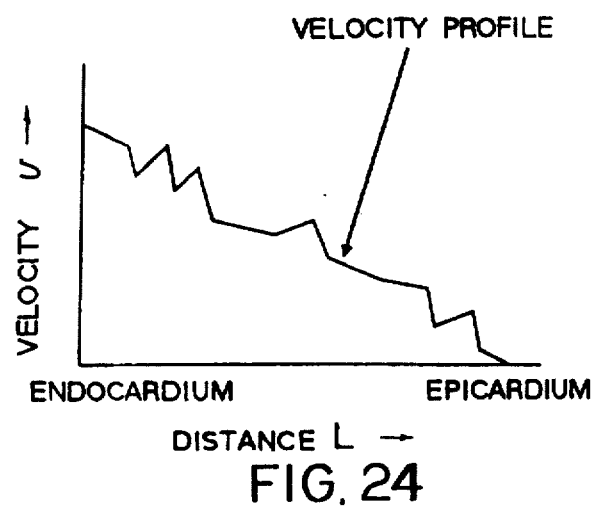
FIG. 24 shows an example of a velocity profile concerning a segment.
Figure 25:
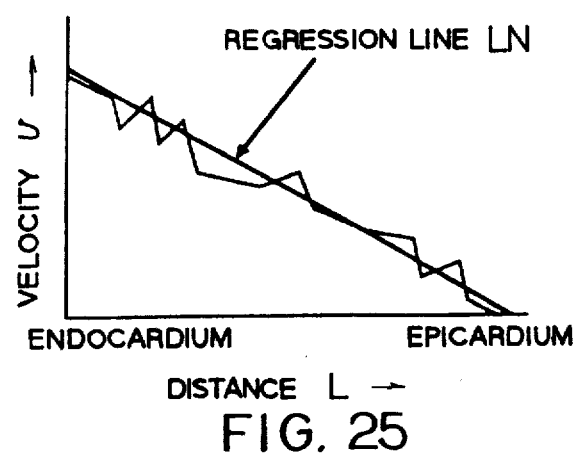
FIG. 25 shows an average velocity gradient concerning a segment.

At step S64, a velocity gradient (average slope) is computed using the velocities detected on each segment at step S63. The relationship between the distances between the endocardium and epicardium and the velocities detected at step S63 is expressed, for example, as shown in FIG. 24. In the profile representing a velocity gradient, a slope is seen inclining from the endocardium toward the epicardium. Besides, velocity variations are observed. At step S64, an average slope (See a regression line LN in FIG. 23) is calculated using a method of least squares in order to ensure a better understanding despite velocity variations. The average slope is computed for each of the segments defined along the whole circumference of an object region.

At step S65, the average slope associated with each of the segments and computed at step S64 is converted into brightness levels. For converting average slopes into brightness levels, a method of using a preprogrammed brightness table as a look-up table or any other method is used to convert a larger average slope into brightness levels so that there will be a larger difference in brightness over the distance from the endocardium to epicardium.

The resultant brightness data is supplied together with associated position information to the image data synthesizer 18 at step S66.

Figure 26:
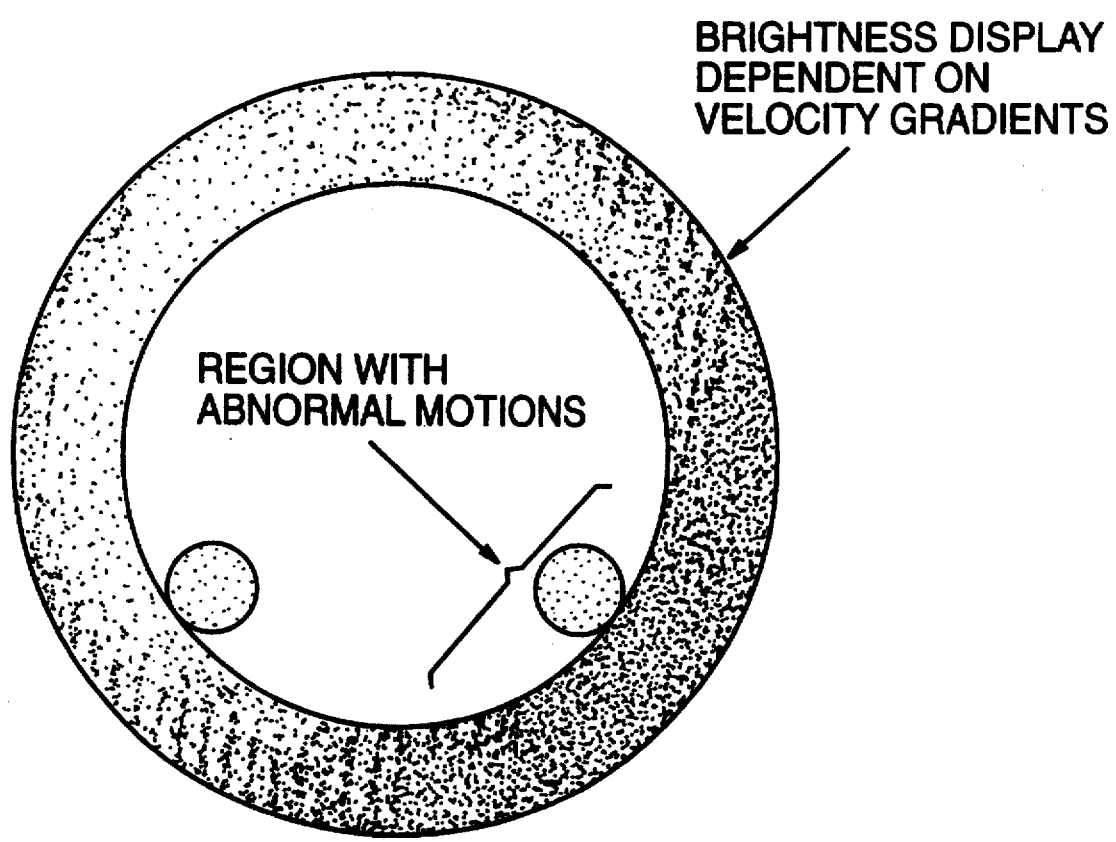
FIG. 26 shows an example of a two-dimensional image mapped according to velocity gradients transformed into brightness levels.

As a result, an image with various brightness levels shown in, for example, FIG. 26 is displayed on the display 19. In this case, the smaller the average slope associated with a segment linking an endocardium and epicardium is, the smaller a difference in brightness between the endocardium and epicardium becomes. In the brightness image of FIG. 26, it is seen that there is almost no difference in brightness between the right lower portions of the endocardium and epicardium. This means that the average slope associated with the right lower portions is almost zero. The portions are assessed as a region of motion anomaly in which the kinetic function of the cardiac muscle is degraded locally due to myocardial infarction or the like. Thus, according to this embodiment, a region with an abnormal kinetic function can be visually distinguished from a region with a normal one depending on the degree of a difference in brightness. The diagnostic ultrasound system of this embodiment can offer excellent diagnostic ability.

Various variants can be made relative to this embodiment.

To begin with, a variant of step S64 will be described. In the velocity profile associated with each segment (See FIG. 24), a slope α of a minute length of the profile is calculated by differentiating a velocity v by a distance L and used instead of the average slope.

$$\alpha = dv/dL$$

At step S65, slopes of minute lengths are converted into brightness levels. Two-dimensional brightness display, which is dependent on velocity gradients, is achieved similarly to the one in FIG. 26. With the display dependent on velocity gradients of minute lengths, localized myocardial anomaly can be identified readily and accutately.

Figure 22:
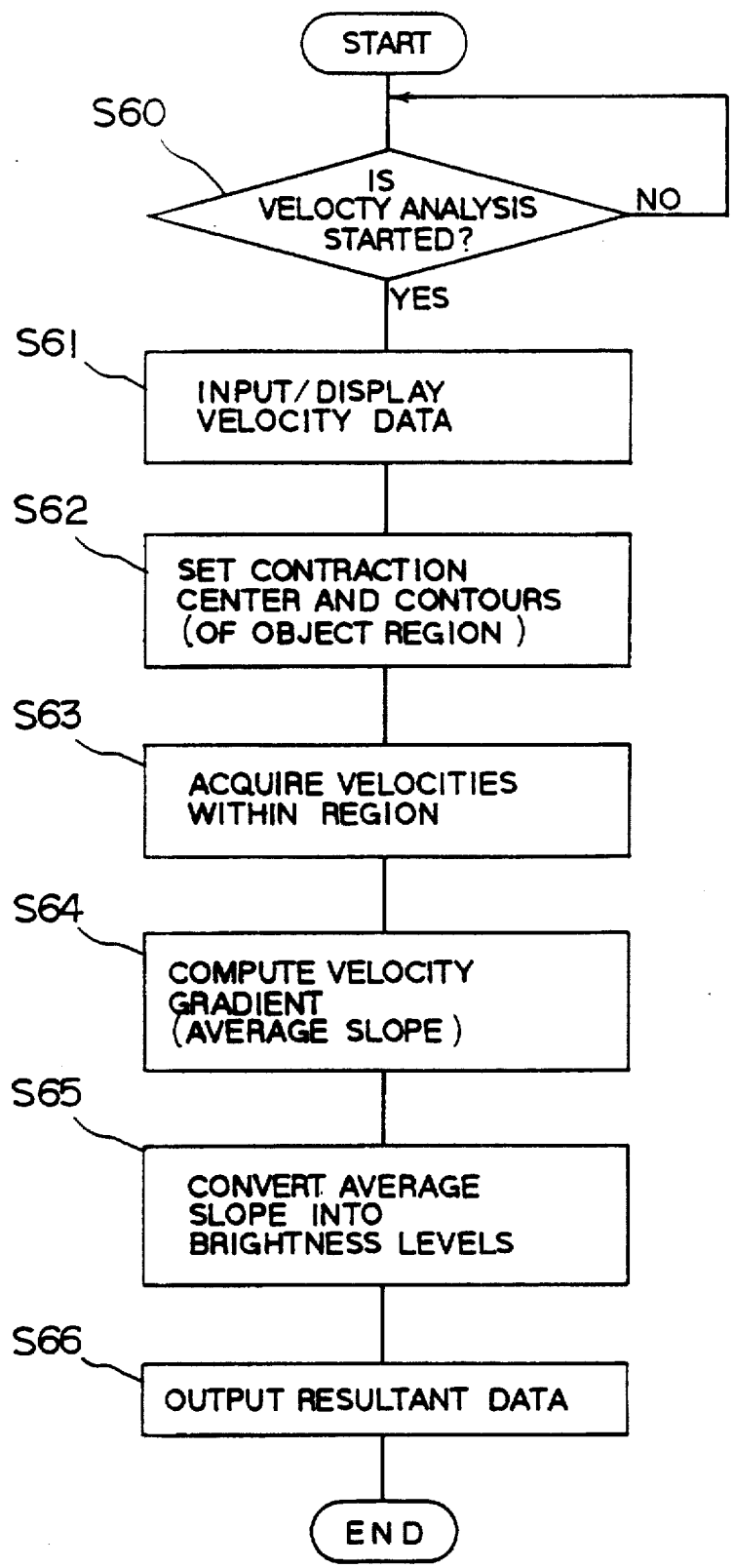
FIG. 22 is a simplified flowchart describing a sequence performed by a velocity analyzer in the sixth embodiment.
Figure 27:
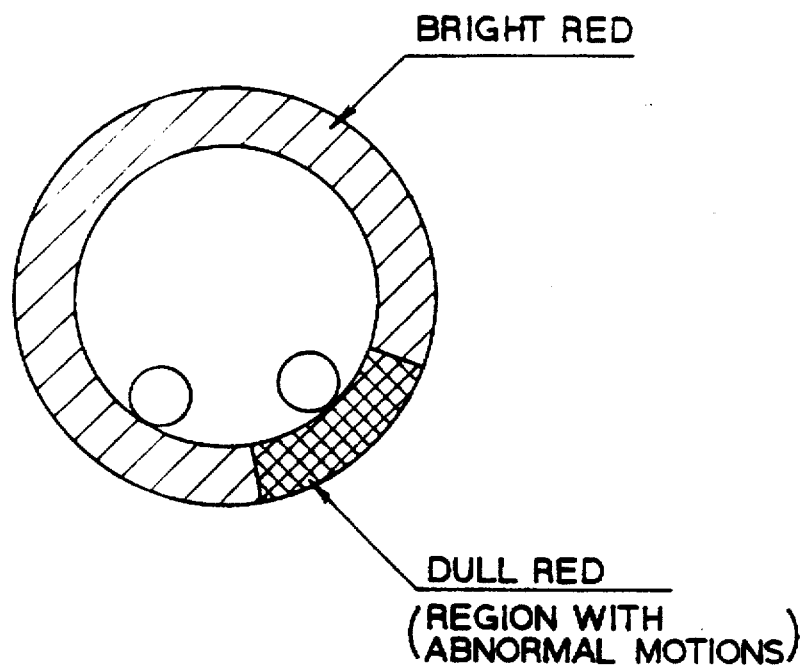
FIG. 27 shows an example of an image mapped according to velocity gradients in a variant.

Secondary, variants of rendering average slopes, which are computed at step S64 in FIG. 22, and associated with segments each linking an endocardium and epicardium will be described in conjunction with FIGS. 27 and 28. According to the variant in FIG. 27, average slopes are discriminated with respect to a given threshold at step S65 succeeding step S64. Average slopes that are lower than the threshold are associated with color data representing dull red. Average slopes that exceed the threshold are associated with color data representing bright red. In a resultant image of the cardiac muscle, as shown in FIG. 27, a portion corresponding to a region of motion anomaly is colored in dull red.

Figure 28:
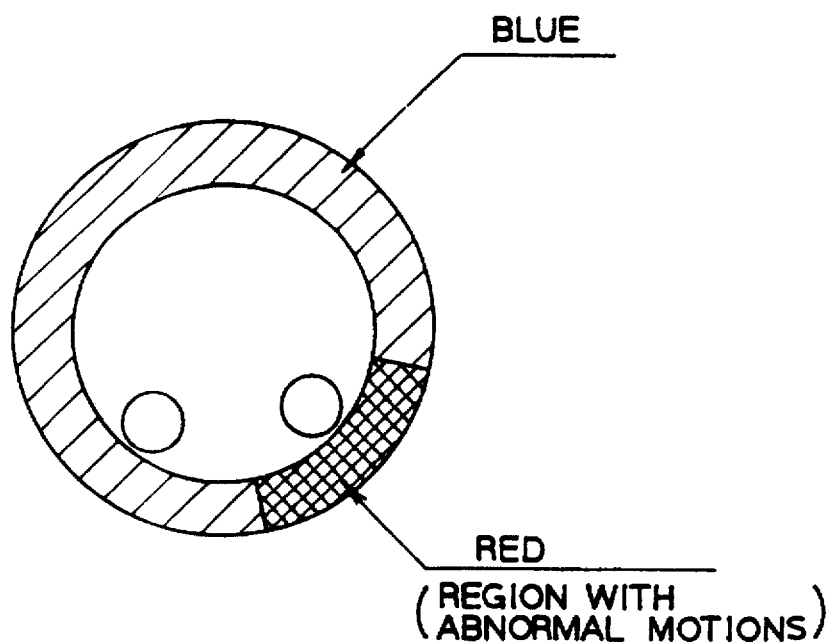
FIG. 28 shows an example of an image mapped according to velocity gradients in another variant.

Likewise, according to the variant in FIG. 28, a red tone is allotted to segments whose associated average slopes are lower than a threshold. A blue tone is allotted to segments whose associated average slopes exceed the threshold. In a resultant image of the cardiac muscle, as shown in FIG. 28, a portion corresponding to a region of motion anomaly is colored in red.

As mentioned above in conjunction with FIGS. 27 and 28, a region with normal motions and a region with abnormal motions can be displayed according to binary representation. These variants have the advantage of making the region with abnormal motions visually discernible. The binary representation in FIG. 27 or 28 can be adapted to the aforesaid technique in which a slope α(=dv /dL) of each minute length Δ L of a profile corresponding to each segment is calculated.

Seventh Embodiment

The seventh embodiment of the present invention will be described in conjunction with FIGS. 1, 26, 29, and 30. This embodiment is, similarly to the sixth embodiment and its variants, concerned with analysis and display of a velocity gradient. An object of this embodiment is to provide a diagnostic ultrasound system making it possible to assess motion ability with higher precision without the particular necessity of defining the contour of an object tissue.

A diagnostic ultrasound system in which the seventh embodiment is implemented has the same configuration as the one shown in FIG. 1. The velocity analyzer 26 executes the sequence described in FIG. 29.

When analysis is commanded (when determination is made in the affirmative at step S70), the velocity analyzer 26 inputs velocity data representing a two-dimensional mapping of velocities on a scanned tomographic layer of, for example, the cardiac muscle from the DSC 24, and displays the velocity data as a two-dimensional mapping image on the display 19 at step S71.

Figure 30:
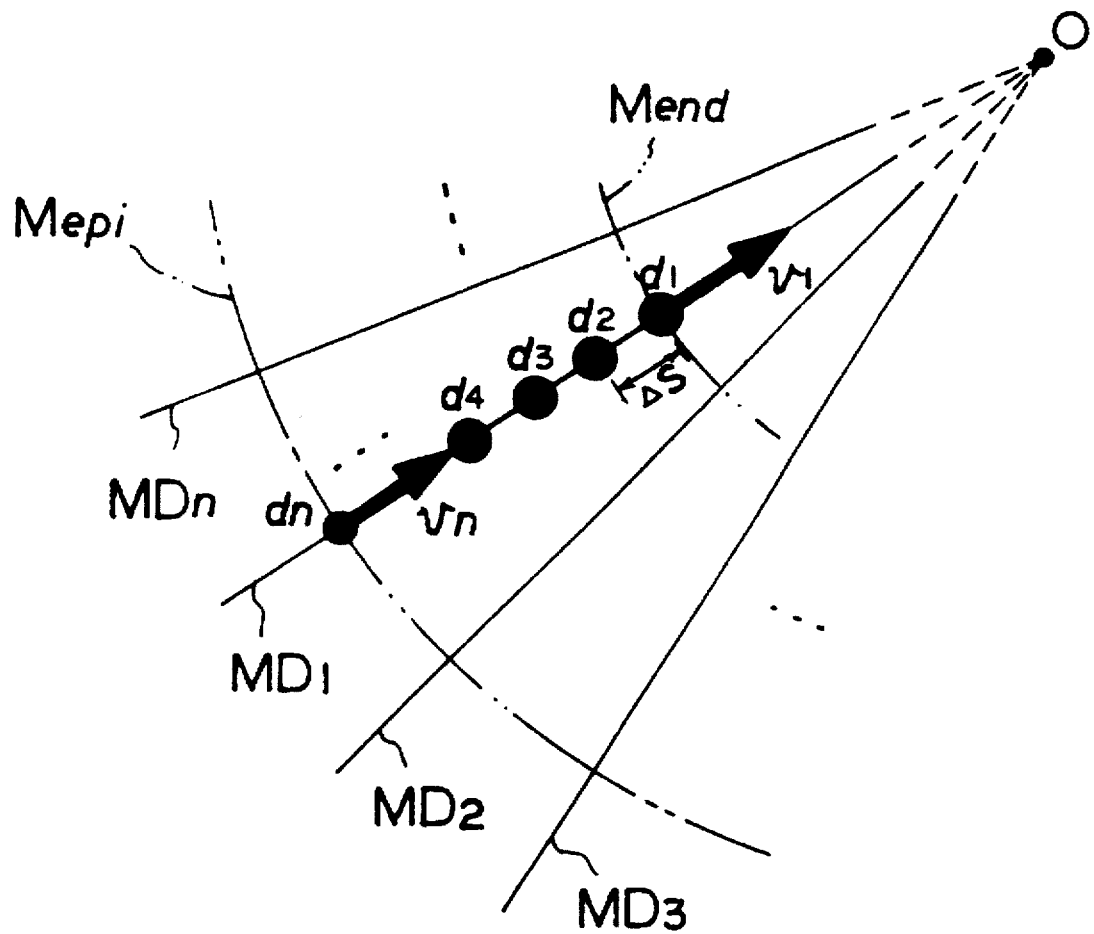
FIG. 30 is an explanatory diagram showing setting of microscopic sections on segments along motion directions for obtaining velocity gradients.
Figure 31:
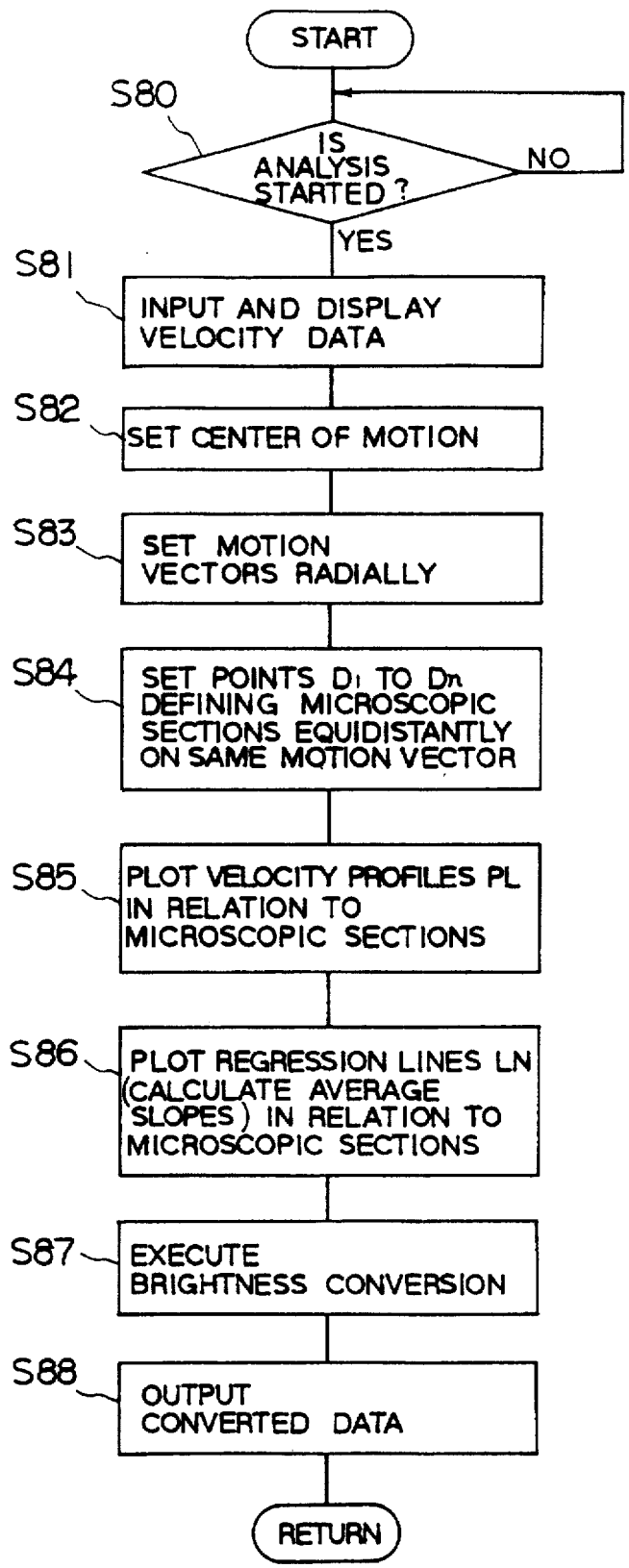
FIG. 31 is a simplified flowchart describing a sequence performed by a velocity analyzer in the eighth embodiment.

Control is then passed to step S72. The center O of myocardial contraction and distention (or of the systolic and diastolic motions of the cardiac muscle) is automatically set as shown in FIG. 30 using a known technique. The center setting may be carried out manually.

Control is then passed to step S73. Segments $MD_1$ to $MD_n$, which represent the directions of motions (two-dimensional vectors on the tomographic layer) and extend radially with respect to the center O of contraction and distention, are set, as shown in FIG. 30, fully around the center O and within the lengths covering the cardiac muscle. In FIG. 30, virtual lines Mend and Mepi are lines indicating the estimated contours of the endocardium and epicardium on a screen. An operator should merely estimate positions on the contours of the endocardium Mend and epicardium Mepi on a screen, and designate the radial segments $MD_1$ to $MD_n$ passing through the positions on the contours of the epicardium and endocardium.

After the above work is completed, a plurality of points $d_1$ to $d_n$ that divide each of the segments $MD_1$ to $MD_n$ equidistantly into a plurality of microscopic sections $\Delta s$ are determined. The points $d_1$ to $d_n$ should be points of coordinates with which each of the segments $MD_1$ to $MD_n$ can be divided into microscopic sections $\Delta s$ ($=d_{n-1}-d_n$), and may have any spacing between adjoining ones. As long as appropriate display ability can be ensured for each microscopic section of an object tissue (which is, in this example, the cardiac muscle), the object of the present invention can be accomplished. Therefore, the length of a microscopic section $\Delta s$ may correspond to, for example, a spacing between adjoining pixels or a distance covering a given number of pixels.

After completing setting of the microscopic sections $\Delta s$, the velocity analyzer 26 passes control to step S75. The velocity analyzer 26 then selects absolute velocities $V_1$ to $V_n$, which are associated with the points $d_1$ to $d_n$ defining the microscopic sections $\Delta s$, from the velocity data for each of the segments $MD_1$ to $MD_n$ indicating the directions of motions. At step S76, differences $S_i$ are calculated according to the expression below.

$$S_i=V_i-V_{i+1} \text{ (where i=1 to n-1)}$$

Thus, differences (equivalent to differential values) between absolute velocities associated with adjoining microscopic sections $\Delta s$ are calculated one after another.

Thereafter, the differences $S_i$ relative to the segments $MD_1$ to $MD_n$ are converted into brightness levels (step S77). The brightness conversion is carried out by, for example, referencing a preprogrammed brightness table. The brightness table contains brightness data that represents lower brightness levels in one-to-one correspondence to smaller differences $S_i$ and higher brightness levels in one-to-one correspondence to larger differences $S_i$. Converted brightness data is then fed to the image data synthesizer 18 together with position data or the like (step S78).

Through the foregoing sequence, a two-dimensional distribution image concerning velocities of myocardial motions appears, similarly to the one in FIG. 26, on the display 19. When myocardial infarction or the like occurs, motion capacity in a certain spatial range diminishes due to tissular necrosis. In this embodiment, a difference between adjoining regions whose motions are considered to be oriented in the same direction is calculated, and then brightness is rendered on the basis of the difference. To be more specific, when motion ability is degraded, each microscopic region is displayed with low brightness dependent on the degree of the degradation or achromatically. When motions are vigorous, each microscopic region is displayed with high brightness dependent on the extent of the vigorousness. This embodiment can display the motion ability of each microscopic region of the myocardial tissue with higher definition than the aforesaid sixth embodiment. Moreover, this embodiment enables more reliable assessment of motion ability.

In this embodiment, the segments $MD_1$ to $MD_n$ are set manually or automatically so that they will outreach a myocardial area. Outreaching portions of the segments $MD_1$ to $MD_n$ are associated with a zero velocity and therefore displayed achromatically in a two-dimensional distribution image concerning myocardial motion velocities. An operator should merely designate segments of a given length that is larger than a normal myocardial size without very much concern about a myocardial area. Unlike the sixth embodiment, the myocardial contour need not be defined. Computation required for contour definition can be omitted, thus lightening computational load.

Eighth Embodiment

The eighth embodiment of the present invention will be described in conjunction with FIGS. 1, 26, 31, and 32. Similarly to the seventh embodiment, this embodiment is concerned with reliable analysis and high-definition display of a velocity gradient. An object of this embodiment is to provide a diagnostic ultrasound system obviating the necessity of defining the contour of an object tissue.

A diagnostic ultrasound system in which the eighth embodiment is implemented has the same configuration as the one shown in FIG. 1. The velocity analyzer 26 executes the sequence described in FIG. 31.

Figure 29:
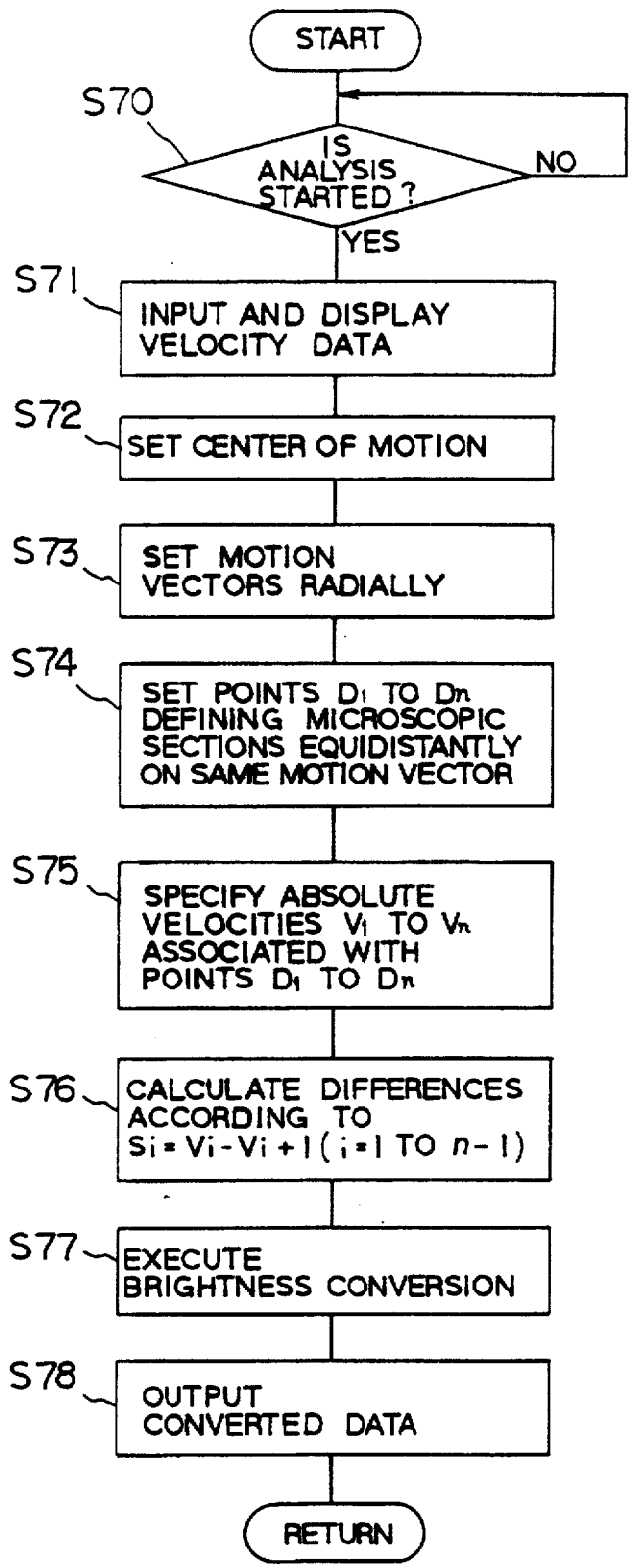
FIG. 29 is a simplified flowchart describing a sequence performed by a velocity analyzer in the seventh embodiment.

When analysis is commanded (when determination is made in the affirmative at step S80), the velocity analyzer 26 executes steps similar to steps S71 to S74 described in FIG. 29 (steps S81 to S84). Consequently, a plurality of points $d_1$ to $d_n$, which divide each of segments $MD_1$ to $MD_n$ into microscopic sections $\Delta L$, are specified on each of the segments $MD_1$ to $MD_n$ (See FIG. 32A). The points $d_1$ to $d_n$ should be points of coordinates defining the microscopic sections $\Delta L$ appropriately. The points $d_1$ to $d_n$ may have any spacing between adjoining ones but may not necessarily be set equidistantly.

After completing setting of the microscopic sections $\Delta L$, the velocity analyzer 26 passes control to step S85. Velocity profiles $PL_1$ to $PL_n$ are plotted as shown in FIG. 32B in relation to the microscopic sections $\Delta L$ on each of the segments $MD_1$ to $MD_n$ indicating the directions of motions. At step S86, regression lines $LN_1$ to $LN_n$ expressing average slopes are, as shown in FIG. 32B, plotted in relation to the velocity profiles $PL_1$ to $PL_n$ according to the method of least squares.

The average slopes (of the regression lines $LN_1$ to $LN_n$) derived from the velocity profiles $PL_1$ to $PL_n$ are converted into brightness levels (step S87). The brightness conversion is carried out by, for example, referencing a preprogrammed brightness table. Smaller slopes are converted into lower brightness levels, and larger slopes are converted into higher brightness levels. Converted brightness data is fed to the image data synthesizer 18 together with associated position data or the like (step S88).

Through the foregoing sequence, a two-dimensional mapping image concerning velocities of myocardial motions is, similarly to the one in FIG. 26, displayed with different brightness levels on the display 19. This results in a brightness image or an image with the different brightness levels that reflect average slopes concerning velocities within microscopic sections oriented possibly in the same direction. Supposing that motion ability is degraded due to myocardial infarction, each microscopic section is displayed with low brightness dependent on the degree of the degradation or achromatically. By contrast, when motions are vigorous, each microscopic section is displayed with high brightness dependent on the extent of the vigorousness. Similarly to the seventh embodiment, this embodiment permits high-definition display and reliable assessment of the kinetic ability of the myocardial tissue in units of a microscopic section.

The method of least squares is used to calculate average slopes on the basis of the velocity profiles $PL_1$ to $PL_n$ related to the microscopic sections. Influence of an error of an average slope attributable to velocity variations can therefore be eliminated. Even in this embodiment, all that an operator must perform is to designate segments $MD_1$ to $MD_n$ of an appropriate length so that the segments will be converged at a center O of contraction and distention. Similarly to the seventh embodiment, the myocardial contour need not be defined. Computation required for contour definition can therefore be omitted. This results in a lightened computational load.

In the seventh and eighth embodiments, a B-mode tomographic image may be used to produce two-dimensional distribution data concerning motion velocities of a tissue. The image display technique described in conjunction with FIG. 27 or 28 may be adapted to the system of the seventh or eighth embodiment.

In the aforesaid embodiments, an image on which a tissue Doppler image of a particular cardiac muscle is superposed is a B-mode tomographic image, and an object to be evaluated is the heart. The present invention is not restricted to the image or object. Alternatively, the B-mode image may be replaced with an M-mode image (in this case, the components required for producing a B-mode image are replaced with those required for producing an M-mode image). Vascular walls may be evaluated on behalf of the cardiac muscle (in this case, the cut-off frequency of the filter 21 is optimized for studies of vascular walls). Furthermore, a tissue Doppler image may not be superposed on the B-mode image or M-mode image but may be displayed solely.

As described so far, in a diagnostic ultrasound system of the present invention, velocities of motions made by a tissue (for example, the cardiac muscle or vascular walls) that acts to produce motion in a living body are detected to create a velocity distribution concerning a section that contains the tissue, and motion velocities detected within a plurality of local regions (for example, regions defined with two ROIs) and read from the velocity distribution are used to analyze the kinetic state of the tissue (for example, a difference in velocity and a ratio of velocities) and display it. The velocity analysis is repeated time-sequentially in real time. Curves expressing time-passing changes of analysis data are displayed. Moreover, two-dimensional velocity gradients are computed using the velocity distribution, and a distribution of gradients is displayed as a two-dimensional image in appropriate form (for example, in the form of an image with various brightness levels). The kinetic state of an organ (tissue) in a region to be diagnosed can be assessed readily merely by viewing a display screen. Hypofunction or anomaly of the organ can be assessed quantitatively, highly precisely, and quickly. The diagnostic ultrasound system of the present invention can be widely adopted to evaluate the cardiac muscle, vascular walls, or any other locomotorium having a contraction center. Furthermore, the heart need not be stressed for the purpose of evaluation. The diagnostic ultrasound system therefore causes no patient discomfort and thus proves a well-acceptable modality.

What is claimed is:

1. A diagnostic ultrasound system for examining tissue of an object using an ultrasonic beam signal, the system comprising:

means for detecting tissue motion velocities at a plurality of sampling points in a section of the object scanned by the ultrasonic beam;

means for producing a single frame of two-dimensionally mapped velocity data based on the detected tissue motion velocities;

means for obtaining plural sets of velocity data indicating properties of plural local regions in the single frame of the two-dimensionally mapped velocity data;

means for analyzing a motion state of the tissue on the basis of the plural sets of velocity data; and means for displaying analysis results of the tissue motion state.

2. The system of claim 1, wherein the velocity detecting means comprises a scanning means for transmitting the ultrasonic beam toward the tissue to acquire a Doppler shifted echo according to a pulsed Doppler technique.

3. The system of claim 2, wherein the velocity detecting means further comprises means for calculating a Doppler shift signal from the echo by frequency analysis and calculating for each of the sampling points an absolute velocity of the tissue motion.

4. The system of claim 2, wherein the producing means includes means for extracting contours of the tissue from the two-dimensionally mapped velocity data and correction means for correcting, on the basis of an angle difference between a direction of the ultrasonic beam and a motion direction of the tissue, the two-dimensionally mapped velocity data being delineated by the extracted contours.

5. The system of claim 1, wherein the obtaining means comprises:

map displaying means for displaying a two-dimensional velocity-mapping image using the single frame of the two-dimensionally mapped velocity data, means for setting the plural local regions on the displayed two-dimensional velocity-mapping image, and means for calculating velocity values from the plural sets of velocity data in connection with each of the plural local regions; and wherein the motion state analyzing means comprises a further calculating means for calculating an index indicative of the tissue motion state using the calculated velocity values.

6. The system of claim 5, wherein the velocity values calculating means includes means that averages a plurality of local velocity values into a typical velocity value for each of the sets of velocity data, the plurality of local velocity values included in each of the local regions set on the two-dimensional velocity-mapping image.

7. The system of claim 6, wherein the tissue is either one of a cardiac muscle and a vascular wall of the object.

8. The system of claim 7, wherein the plurality of local regions set by the setting means are two regions of interest (ROIs) separately set on either one of the cardiac muscle and the vascular wall.

9. The system of claim 8, wherein the setting means includes means that separately sets the two ROIs on an endocardium and an epicardium of the cardiac muscle.

10. The system of claim 8, wherein the setting means includes means that separately sets the two ROIs on a tunica intima and a tunica externa of the vascular wall.

11. The system of claim 8, wherein the index is at least one of a velocity difference between the typical velocity values of the two ROIs, a velocity ratio between the typical velocity values of the two ROIs, and a velocity gradient between the two typical velocity values of the two ROIs.

12. The system of claim 5, wherein the setting means is a means that automatically sets the plurality of local regions.

13. A diagnostic ultrasound system for examining tissue of an object using an ultrasonic beam, the system comprising:

means for detecting in real time tissue motion velocities at a plurality of sampling points in a section of the object scanned by the ultrasonic beam;

means for producing in time sequence a plurality of frames of two-dimensionally mapped velocity data based on the detected tissue motion velocities;

means for obtaining plural sets of velocity data respectively indicating properties of a plurality of local regions in each of the plural frames of the two-dimensionally mapped velocity;

means for analyzing a motion state of the tissue on the basis of the plural sets of velocity data obtained for each of the plurality of frames of the two-dimensionally mapped velocity data means for transforming the analyzed tissue motion state into corresponding time-dependent velocity data; and means for displaying the time-dependent velocity data.

14. The system of claim 13, wherein the obtaining means comprises:

map displaying means for displaying a two-dimensional velocity-mapping image using one of the plural frames of two-dimensionally mapped velocity data;

means for setting the plurality of local regions on the displayed two-dimensional velocity-mapping image;

means for automatically causing the plurality of local regions to lock-on over the plural frames of two-dimensionally mapped velocity data; and data calculating means for calculating values of the plural sets of velocity data in connection with each of the plurality of local regions locked-on in each of the plural frames of two-dimensionally mapped velocity data, and wherein the motion state analyzing means includes an index calculating means for calculating an index indicative of the tissue motion state using the calculated velocity values.

15. The system of claim 13, wherein the obtaining means comprises:

map displaying means for displaying a two-dimensional velocity-mapping image using one of the plural frames of two-dimensionally mapped velocity data, means for setting a single region including the plurality of local regions and a desired tissue motion range on the displayed two-dimensional velocity-mapping image, means for calculating a velocity histogram of the velocity data within the single region for each of the plural frames of two-dimensionally mapped velocity data; and wherein the motion state analyzing means comprises means for calculating an index indicative of the tissue motion states for all of the plural frames of two-dimensionally mapped velocity data, using the calculated velocity histograms.

16. The system of claim 15, wherein the tissue is a cardiac muscle.

17. The system of claim 16, wherein the motion state analyzing means comprises:

means for acquiring the plural frames of two-dimensionally mapped velocity data from the producing means at a cardiac timing when a motion velocity of an endocardium of the cardiac muscle reaches a maximum velocity value.

18. The system of claim 17, wherein the index calculating means comprises a velocity specifying means for respectively specifying, as velocities in the plurality of local regions, two average velocities in a maximum velocity range and minimum velocity range in the calculated velocity histogram, and an index computing means for computing the index on the basis of the two average velocities.

19. The system of claim 18, wherein the index computed by the index computing means is at least one of a velocity difference between the two average velocities, a velocity ratio between the two average velocities, and a velocity gradient between the two average velocities.

20. A diagnostic ultrasound system for examining tissue of an object using an ultrasonic beam, the system comprising:

means for detecting tissue motion velocities at a plurality of sampling points in a section of the object scanned by the ultrasonic beam;

means for producing a single frame of two-dimensionally mapped velocity data in the section on the basis of the detected velocities;

means for providing a plurality of tissue motion directions on the single frame of the two-dimensionally mapped velocity data, means for calculating a plurality of velocity gradients along the plurality of directions provided on the two-dimensionally mapped velocity data, and means for displaying the velocity gradients as a two-dimensional image.

21. The system of claim 20, wherein the tissue is a cardiac muscle.

22. The system of claim 20, wherein the directions providing means comprises:

velocity map displaying means for displaying a two-dimensional velocity-mapping image using the two-dimensionally mapped velocity data, means for specifying endocardium and epicardium contours of the cardiac muscle on the displayed two-dimensional velocity-mapping image, and wherein the velocity gradients calculating means includes means for obtaining positions of a plurality of segments connecting the endocardium and epicardium contours to each other in the shortest length and an average velocity gradient for each of the plurality of segments.

23. The system of claim 22, wherein the velocity gradients displaying means comprises:

a means for forming brightness data corresponding to the average velocity gradients and a means for displaying the brightness data in one-to-one correspondence to positions of the plurality of segments.

24. The system of claim 22, wherein the velocity gradients displaying means comprises:

means for producing hue data corresponding to the average velocity gradients and a means for displaying the hue data in one-to-one correspondence to positions of the plurality of segments.

25. The system of claim 22, wherein the positions obtaining means includes means that computes the average velocity gradients using a least square method.

26. The system of claim 20, wherein the directions providing means comprises:

velocity map displaying means for displaying a two-dimensional velocity-mapping image using the two-dimensionally mapped velocity data, and a direction specifying means for specifying a plurality of tissue motion directions on the displayed two-dimensional velocity-mapping image, and wherein the velocity gradients calculating means includes means for calculating positions of a plurality of minute lengths along each of the tissue motion directions and differences in tissue motion velocities between adjoining minute lengths aligning the minute lengths along each tissue motion direction.

27. The system of claim 26, wherein the velocity gradients displaying means comprises:
  means for producing brightness data respectively corresponding to each the plurality tissue motion velocity differences in each tissue motion direction and
  a means for displaying the brightness data in one-to-one correspondence to positions of the minute lengths over the plurality of tissue motion directions.

28. The system of claim 26, wherein the velocity gradients displaying means comprises:
  a means for producing hue data corresponding to the plurality of tissue motion velocity differences in every tissue motion direction and
  a means for displaying the hue data in one-to-one correspondence to positions of the minute lengths over the plurality of tissue motion directions.

29. The system of claim 26, wherein the direction specifying means includes a means that specifies not only a motion center on the displayed two-dimensional velocity-mapping image, but also a plurality of radial segments extending from a motion center and exceeding a displayed tissue range, the plurality of radial segments being respectively indicative of the plurality of tissue motion directions.

30. The system of claim 20, wherein the directions providing means comprises:
  velocity map displaying means for displaying a two-dimensional velocity-mapping image using the two-dimensionally mapped velocity data;
  means for specifying a plurality of motion directions of the tissue on the displayed two-dimensional velocity-mapping image, and
  wherein the velocity gradient calculating means comprises:
    profile calculating means for calculating positions of a plurality of minute lengths along each of the tissue motion directions and velocity profiles in each minute length, and
    means for calculating an average velocity gradient of the velocity profile of each minute length in each of the tissue motion directions.

31. The system of claim 30, wherein the velocity gradients displaying means comprises:
  a means for producing brightness data corresponding to the plurality of average velocity gradients in every tissue motion direction and
  a means for displaying the brightness data in one-to-one correspondence to the positions of the plural minute lengths in every tissue motion direction.

32. The system of claim 30, wherein the velocity gradients displaying means comprises:
  a means for producing hue data corresponding to the plurality of average velocity gradients in every tissue motion direction, and
  a means for displaying the hue data in one-to-one correspondence to the positions of the plurality of minute lengths in every tissue motion direction.

33. The system of claim 30, wherein the gradient calculating means is a means that calculates the average velocity gradient using a least square method.

34. The system of claim 30, wherein the direction specifying means includes means that specifies not only a motion center on the displayed two-dimensional velocity-mapping image, but also a plurality of radial segments extending from the motion center and exceeding a displayed tissue range, the plurality of radial segments being respectively indicative of the plurality of tissue motion directions.

35. A method of imaging tissue of an object under examination using an ultrasonic beam the method comprising the steps of:
  detecting velocities of tissue motion at a plurality of sampling points in a section of the object scanned by the ultrasonic beam;
  producing a single frame of two-dimensionally mapped velocity data in the section based on the detected tissue motion velocities;
  obtaining plural sets of velocity data respectively indicating properties of a plurality of local regions in the single frame of the two-dimensionally mapped velocity data;
  analyzing a motion state of the tissue on the basis of velocity values of the plural sets of velocity data; and
  displaying analysis results of the motion state.

36. A method of imaging tissue of an object under diagnostic examination using an ultrasonic beam, the method comprising the steps of:
  detecting in real time velocities of tissue motion at a plurality of sampling points in a section of the object scanned by the ultrasonic beam;
  producing, in time sequence, plural frames of two-dimensionally mapped velocity data from the detected tissue motion velocities;
  obtaining plural sets of velocity data individually reflecting properties of a plurality of local regions in each of the plural frames of the two-dimensionally mapped velocity data;
  analyzing a motion state of the tissue on the basis of the plural sets of velocity data obtained for each of the plural frames of the two-dimensionally mapped velocity data;
  transforming analyzed results of the tissue motion state into corresponding time-dependent velocity data; and
  displaying the time-dependent velocity data.

37. A method of imaging tissue of an object under diagnostic examination using an ultrasonic beam, the method comprising the steps of:
  detecting velocities of tissue motion at a plurality of sampling points in a section of the object scanned by the ultrasonic beam;
  producing a single frame of two-dimensionally mapped velocity data on the basis of the detected velocities;
  indicating tissue motion directions in the single frame of two-dimensionally mapped velocity data;
  calculating velocity gradient data of the tissue motions indicated in the two-dimensionally mapped velocity data; and
  displaying the velocity gradient data in a two-dimensional image.

* * * * *

UNITED STATES PATENT AND TRADEMARK OFFICE
CERTIFICATE OF CORRECTION

PATENT NO. : 5,615,680
DATED : April 01, 1997
INVENTOR(S) : Akihiro SANO

It is certified that error appears in the above-indentified patent and that said Letters Patent is hereby corrected as shown below:

Claim 13, column 23, line 10, after "velocity", insert --data--.

Claim 27, column 25, line 10, after "plurality", insert --of--.

Claim 35, column 26, line 11, after "beam", insert --,--.

Signed and Sealed this

Eighth Day of July, 1997

Attest:

Attesting Officer

BRUCE LEHMAN

Commissioner of Patents and Trademarks